(12) United States Patent
Connor

(10) Patent No.: US 10,458,845 B2
(45) Date of Patent: Oct. 29, 2019

(54) MOBILE DEVICE FOR FOOD IDENTIFICATION AN QUANTIFICATION USING SPECTROSCOPY AND IMAGING

(71) Applicant: Robert A. Connor, St. Paul, MN (US)

(72) Inventor: Robert A. Connor, St. Paul, MN (US)

(73) Assignee: Medibotics LLC, St. Paul, MN (US)

( * ) Notice: Subject to any disclaimer, the term of this patent is extended or adjusted under 35 U.S.C. 154(b) by 229 days.

(21) Appl. No.: 15/879,581

(22) Filed: Jan. 25, 2018

(65) Prior Publication Data

US 2018/0149519 A1 May 31, 2018

Related U.S. Application Data

(63) Continuation-in-part of application No. 15/004,427, filed on Jan. 22, 2016, now abandoned, which is a continuation-in-part of application No. 13/901,131, filed on May 23, 2013, now Pat. No. 9,536,449, and a continuation-in-part of application No. 14/132,292, filed on Dec. 18, 2013, now Pat. No. 9,442,100, and a continuation-in-part of application No. 14/449,387, filed on Aug. 1, 2014, now abandoned, and a continuation-in-part of application No. 14/948,308, filed on Nov. 21, 2015, now abandoned, which is a continuation-in-part of application No. 13/901,099, filed on May 23, 2013, now Pat. No. 9,254,099, and
(Continued)

(51) Int. Cl.
*G01J 3/02* (2006.01)
*G06T 1/00* (2006.01)
*G01N 21/25* (2006.01)
*G01N 33/02* (2006.01)
*G01N 21/15* (2006.01)
*G01N 21/3563* (2014.01)

(52) U.S. Cl.
CPC ........... *G01J 3/0272* (2013.01); *G01J 3/0202* (2013.01); *G01J 3/0291* (2013.01); *G01N 21/255* (2013.01); *G01N 33/02* (2013.01); *G06T 1/0007* (2013.01); *G01N 21/15* (2013.01); *G01N 21/3563* (2013.01); *G01N 2201/0221* (2013.01); *G01N 2201/129* (2013.01); *G06T 2207/30128* (2013.01)

(58) Field of Classification Search
CPC ...... G01N 33/02; G01N 21/255; G01N 21/15; G01N 21/3563; G01N 2201/0221; G01N 2201/129; G01J 3/0291; G01J 3/0202; G01J 3/0272; G06T 1/0007; G06T 2207/30128
See application file for complete search history.

(56) References Cited

U.S. PATENT DOCUMENTS

| 8,355,875 B2 | 1/2013 | Hyde et al. |
| 9,198,621 B2 | 12/2015 | Fernstrom et al. |

(Continued)

*Primary Examiner* — Nathan Hillery

(57) ABSTRACT

This invention can be embodied in a mobile device for food identification and quantification with both a spectroscopic sensor and a camera. It can be a handheld food scanner, food probe, smart food utensil, utensil attachment, removable component of a smart watch or wrist band, phone component, or phone accessory. It can provide information on types and quantities of food (and nutrients, chemicals, and microorganisms in that food). It can be wirelessly linked with a wearable device to comprise a system for monitoring and modifying a person's food consumption habits.

3 Claims, 7 Drawing Sheets

Related U.S. Application Data a continuation-in-part of application No. 14/132,292, filed on Dec. 18, 2013, now Pat. No. 9,442,100, which is a continuation-in-part of application No. 15/464,349, filed on Mar. 21, 2017, now Pat. No. 9,968,297, which is a continuation-in-part of application No. 15/136,948, filed on Apr. 24, 2016, now Pat. No. 10,234,942, application No. 15/879,581, which is a continuation-in-part of application No. 15/464,349, filed on Mar. 21, 2017, now Pat. No. 9,968,297, and a continuation-in-part of application No. 14/599,522, filed on Jan. 18, 2015, now Pat. No. 9,814,426, and a continuation-in-part of application No. 14/562,719, filed on Dec. 7, 2014, now Pat. No. 10,130,277, and a continuation-in-part of application No. 14/330,649, filed on Jul. 14, 2014, now abandoned, and a continuation-in-part of application No. 13/797,955, filed on Mar. 12, 2013, now Pat. No. 9,456,916, and a continuation-in-part of application No. 13/523,739, filed on Jun. 14, 2012, now Pat. No. 9,042,596.

(60) Provisional application No. 62/430,667, filed on Dec. 6, 2016, provisional application No. 62/089,696, filed on Dec. 9, 2014, provisional application No. 62/017,615, filed on Jun. 26, 2014, provisional application No. 61/939,244, filed on Feb. 12, 2014, provisional application No. 61/932,517, filed on Jan. 28, 2014, provisional application No. 61/729,494, filed on Nov. 23, 2012.

(56) References Cited

U.S. PATENT DOCUMENTS

| | | | |
|---|---|---|---|
| 9,291,504 | B2 | 3/2016 | Goldring et al. |
| 9,377,396 | B2 | 6/2016 | Goldring et al. |
| 9,383,258 | B2 | 7/2016 | Goldring et al. |
| 9,448,114 | B2 | 9/2016 | Goldring et al. |
| 9,500,523 | B2 | 11/2016 | Goldring et al. |
| 9,562,848 | B2 | 2/2017 | Goldring et al. |
| 9,574,942 | B2 | 2/2017 | Goldring et al. |
| 9,587,982 | B2 | 3/2017 | Goldring et al. |
| 9,717,425 | B2 | 8/2017 | Kiani et al. |
| 2002/0047867 | A1* | 4/2002 | Mault ............... G06F 19/00 715/810 |
| 2002/0099274 | A1* | 7/2002 | Isomura ............ G06F 19/00 600/300 |
| 2005/0020892 | A1* | 1/2005 | Acosta ............... A61B 5/0075 600/316 |
| 2007/0273504 | A1* | 11/2007 | Tran ................. A61B 5/0022 340/539.12 |
| 2009/0012433 | A1 | 1/2009 | Fernstrom et al. |
| 2009/0227877 | A1* | 9/2009 | Tran ................. A61B 5/021 600/483 |
| 2010/0125419 | A1* | 5/2010 | Hyde ................ A47G 23/12 702/19 |
| 2010/0283601 | A1* | 11/2010 | Tai .................. G06Q 50/24 340/539.12 |
| 2011/0106627 | A1* | 5/2011 | LeBoeuf ............ G06F 19/00 705/14.66 |
| 2012/0094258 | A1* | 4/2012 | Langheier .......... G06F 19/3475 434/127 |
| 2012/0290327 | A1* | 11/2012 | Hanlon ............. G06Q 30/0271 705/3 |
| 2013/0085345 | A1* | 4/2013 | Geisner ............. G06Q 30/00 600/300 |
| 2013/0172691 | A1* | 7/2013 | Tran ................. A61B 8/488 600/301 |
| 2013/0245396 | A1* | 9/2013 | Berman ............. G06F 19/3418 600/301 |
| 2013/0267794 | A1 | 10/2013 | Fernstrom et al. |
| 2014/0061486 | A1 | 3/2014 | Bao et al. |
| 2014/0085077 | A1* | 3/2014 | Luna ................. G08B 6/00 340/539.11 |
| 2014/0273858 | A1* | 9/2014 | Panther ............. A61B 5/0002 455/41.2 |
| 2014/0288390 | A1* | 9/2014 | Hong ................ A61B 5/02427 600/301 |
| 2014/0316305 | A1* | 10/2014 | Venkatraman ...... A61B 5/1112 600/595 |
| 2014/0320858 | A1 | 10/2014 | Goldring et al. |
| 2014/0349257 | A1 | 11/2014 | Connor |
| 2015/0036138 | A1 | 2/2015 | Watson et al. |
| 2015/0148632 | A1 | 5/2015 | Benaron |
| 2015/0148636 | A1 | 5/2015 | Benaron |
| 2015/0168365 | A1 | 6/2015 | Connor |
| 2015/0292948 | A1 | 10/2015 | Goldring et al. |
| 2015/0300879 | A1 | 10/2015 | Goldring et al. |
| 2015/0302160 | A1 | 10/2015 | Muthukumar et al. |
| 2015/0355024 | A1 | 12/2015 | Goldring et al. |
| 2016/0033328 | A1 | 2/2016 | Walters |
| 2016/0290863 | A1 | 10/2016 | Goldring et al. |
| 2016/0299061 | A1 | 10/2016 | Goldring et al. |
| 2017/0160131 | A1 | 6/2017 | Goldring et al. |
| 2017/0234729 | A1 | 8/2017 | Goldring et al. |
| 2017/0292908 | A1 | 10/2017 | Wilk et al. |
| 2017/0323057 | A1 | 11/2017 | Karvela et al. |
| 2017/0336319 | A1 | 11/2017 | Hruska et al. |
| 2018/0003558 | A1 | 1/2018 | Goldring et al. |

\* cited by examiner

MOBILE DEVICE FOR FOOD IDENTIFICATION AN QUANTIFICATION USING SPECTROSCOPY AND IMAGING

CROSS-REFERENCE TO RELATED APPLICATIONS

This application:

(A) is a continuation in part of U.S. patent application Ser. No. 15/004,427 by Robert A. Connor entitled "Hand-Held Spectroscopic Sensor with Light-Projected Fiducial Marker for Analyzing Food Composition and Quantity" filed on Jan. 22, 2016 which: (1) was a continuation in part of U.S. patent application Ser. No. 13/901,131 by Robert A. Connor entitled "Smart Watch and Food Utensil for Monitoring Food Consumption" filed on May 23, 2013; (2) was a continuation in part of U.S. patent application Ser. No. 14/132,292 by Robert A. Connor entitled "Caloric Intake Measuring System using Spectroscopic and 3D Imaging Analysis" filed on Dec. 18, 2013; (3) was a continuation in part of U.S. patent application Ser. No. 14/449,387 by Robert A. Connor entitled "Wearable Imaging Member and Spectroscopic Optical Sensor for Food Identification and Nutrition Modification" filed on Aug. 1, 2014; and (4) was a continuation in part of U.S. patent application Ser. No. 14/948,308 by Robert A. Connor entitled "Spectroscopic Finger Ring for Compositional Analysis of Food or Other Environmental Objects" filed on Nov. 21, 2015 which was a continuation in part of U.S. patent application Ser. No. 13/901,099 by Robert A. Connor entitled "Smart Watch and Food-Imaging Member for Monitoring Food Consumption" filed on May 23, 2013, a continuation in part of U.S. patent application Ser. No. 14/132,292 by Robert A. Connor entitled "Caloric Intake Measuring System using Spectroscopic and 3D Imaging Analysis" filed on Dec. 18, 2013, and a continuation in part of U.S. patent application Ser. No. 14/449,387 by Robert A. Connor entitled "Wearable Imaging Member and Spectroscopic Optical Sensor for Food Identification and Nutrition Modification" filed on Aug. 1, 2014; and (B) is a continuation in part of U.S. patent application Ser. No. 15/464,349 by Robert A. Connor entitled "EEG Glasses (Electroencephalographic Eyewear)" filed on Mar. 21, 2017 which: (1) claimed the priority benefit of U.S. Provisional Patent Application 62/430,667 entitled "EEG Glasses and Other Electroencephalographic Eyewear" filed on Dec. 6, 2016; (2) was a continuation in part of U.S. patent application Ser. No. 14/330,649 entitled "Eyewear System for Monitoring and Modifying Nutritional Intake" filed on Jul. 14, 2014 which was a continuation in part of U.S. patent application Ser. No. 13/523,739 entitled "Willpower Watch™—A Wearable Food Consumption Monitor" filed on Jun. 14, 2012, and was a continuation in part of U.S. patent application Ser. No. 13/797,955 entitled "Device for Selectively Reducing Absorption of Unhealthy Food" filed on Mar. 12, 2013 which claimed the priority benefit of U.S. Provisional Patent Application 61/729,494 entitled "Device for Selectively Reducing Absorption of Unhealthy Food" filed on Nov. 23, 2012; (3) was a continuation in part of U.S. patent application Ser. No. 14/562,719 entitled "Willpower Glasses™: A Wearable Food Consumption Monitor" filed on Dec. 7, 2014 which claimed the priority benefit of U.S. Provisional Patent Application 61/932,517 entitled "Nutrode™: Wearable EEG Monitor for Modifying Food Consumption" filed on Jan. 28, 2014; and (4) was a continuation in part of U.S. patent application Ser. No. 15/136,948 entitled "Wearable and Mobile Brain Computer Interface (BCI) Device and Method" filed on Apr. 24, 2016 which was a continuation-in-part of U.S. patent application Ser. No. 14/599,522 entitled "Mobile Wearable Electromagnetic Brain Activity Monitor" filed on Jan. 18, 2015 which, in turn: (a) was a continuation in part of U.S. patent application Ser. No. 14/562,719 entitled "Willpower Glasses™: A Wearable Food Consumption Monitor" filed on Dec. 7, 2014 which claimed the priority benefit of U.S. Provisional Patent Application 61/932,517 entitled "Nutrode™: Wearable EEG Monitor for Modifying Food Consumption" filed on Jan. 28, 2014; (b) claimed the priority benefit of U.S. Provisional Patent Application 61/932,517 entitled "Nutrode™: Wearable EEG Monitor for Modifying Food Consumption" filed on Jan. 28, 2014; (c) claimed the priority benefit of U.S. Provisional Patent Application 61/939,244 entitled "Brainwave-Controlled Eyewear" filed on Feb. 12, 2014; (d) claimed the priority benefit of U.S. Provisional Patent Application 62/017,615 entitled "Nervision™ Integrated Eyewear and EEG Monitor" filed on Jun. 26, 2014; and (e) claimed the priority benefit of U.S. Provisional Patent Application 62/089,696 entitled "Electroencephalographic Eyewear" filed on Dec. 9, 2014; claimed the priority benefit of U.S. Provisional Patent Application 62/160,172 entitled "Hair-Engaging Mobile Brain Activity Monitor" filed on May 12, 2015; claimed the priority benefit of U.S. Provisional Patent Application 62/169,661 entitled "Internet of Thinks (IoT): A Brain Computer Interface (BCI) Using EEG Patterns Associated with the Same Command Across Different Action Modes" filed on Jun. 2, 2015; claimed the priority benefit of U.S. Provisional Patent Application 62/303,126 entitled "Undulating Mobile EEG Monitor Spanning a Portion of the Forehead" filed on Mar. 3, 2016; and claimed the priority benefit of U.S. Provisional Patent Application 62/322,594 entitled "Halo-Style Mobile Electroencephalographic (EEG) Monitor" filed on Apr. 14, 2016.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to mobile devices for analyzing and measuring food.

INTRODUCTION

The United States population has some of the highest prevalence rates of obese and overweight people in the world. Further, these rates have increased dramatically during recent decades. In the late 1990's, around one in five Americans was obese. Today, that figure has increased to around one in three. The prevalence of Americans who are generally overweight is estimated to be as high as two out of three. Despite the considerable effort that has been focused on developing new approaches for preventing and treating obesity, the problem is growing. There remains a serious unmet need for new ways to help people to moderate their consumption of unhealthy food, better manage their energy balance, and lose weight in a healthy and sustainable manner.

Obesity is a complex disorder with multiple interacting causal factors including genetic factors, environmental factors, and behavioral factors. A person's behavioral factors include the person's caloric intake (the types and quantities of food which the person consumes) and caloric expenditure (the calories that the person burns in regular activities and exercise). Energy balance is the net difference between caloric intake and caloric expenditure. Other factors being equal, energy balance surplus (caloric intake greater than caloric expenditure) causes weight gain and energy balance deficit (caloric intake less than caloric expenditure) causes weight loss.

Since many factors contribute to obesity, good approaches to weight management are comprehensive in nature. Proper nutrition and management of caloric intake are key parts of a comprehensive approach to weight management. Consumption of "junk food" that is high in simple sugars and saturated fats has increased dramatically during the past couple decades, particularly in the United States. This has contributed significantly to the obesity epidemic. For many people, relying on willpower and dieting is not sufficient to moderate their consumption of unhealthy "junk food." The results are dire consequences for their health and well-being.

The invention that is disclosed herein directly addresses this problem by helping a person to monitor their nutritional intake. The invention that is disclosed herein is an innovative technology that can be a key part of a comprehensive system that helps a person to reduce their consumption of unhealthy food, to better manage their energy balance, and to lose weight in a healthy and sustainable manner. This invention is a mobile device for food identification and quantification. It can be used as a stand-alone device or wirelessly linked with a wearable device to comprise a system for monitoring and modifying a person's food consumption habits.

REVIEW OF THE MOST RELEVANT ART

There has been considerable progress in the development of handheld spectroscopy sensors during the last decade. A prime example is SCiO made by Consumer Physics. SCiO is an innovative handheld molecular sensor which uses spectroscopy to analyze the composition of nearby objects. It can be used to analyze the composition of food. There are several innovative patents and patent applications by Goldring and others in the Consumer Physics team. The SCiO by itself does not appear to measure food quantity. DietSensor appears to be a software application which can be used with the SCiO spectroscopic sensor and a portable food scale to estimate food quantity. U.S. patents and applications by Goldring et al. include the following.

U.S. patent applications by Goldring et al. 20140320858, "Low-Cost Spectrometry System for End-User Food Analysis" and 20160290863, "Low-Cost Spectrometry System for End-User Food Analysis," and U.S. patents by Goldring et al. U.S. Pat. No. 9,377,396, "Low-Cost Spectrometry System for End-User Food Analysis" and U.S. Pat. No. 9,587,982, "Low-Cost Spectrometry System for End-User Food Analysis" appear to disclose a compact spectrometer which can be used in a phone. It can be used to evaluate food quality. It can comprise a filter, a Fourier transform focusing element, a micro-lens array, and a detector.

U.S. patent applications by Goldring et al. 20150292948, "Spectrometry System with Diffuser," 20150300879, "Spectrometry System with Isolated Optical Paths," 20150355024, "Spectrometry System with Decreased Light Path," 20170234729, "Spectrometry System with Decreased Light Path," and also U.S. patents by Goldring et al. U.S. Pat. No. 9,291,504, "Spectrometry System with Decreased Light Path," U.S. Pat. No. 9,383,258, "Spectrometry System with Filters and Illuminator Having Primary and Secondary Emitters," U.S. Pat. No. 9,448,114, "Spectrometry System with Diffuser Having Output Profile Independent of Angle of Incidence and Filters," U.S. Pat. No. 9,500,523, "Spectrometry System with Diffuser and Filter Array and Isolated Optical Paths," and U.S. Pat. No. 9,574,942, "Spectrometry System with Decreased Light Path" appear to disclose a spectrometer with a plurality of isolated optical paths which allow it to be shorter with increased resolution.

U.S. patent applications by Goldring et al. 20160299061, "Spectrometry Systems, Methods, and Applications" and 20170160131, "Spectrometry Systems, Methods, and Applications" and also U.S. patent by Goldring et al. U.S. Pat. No. 9,562,848, "Spectrometry Systems, Methods, and Applications" appear to disclose a handheld spectrometer which communicates with a database of spectral information to determine attributes of an object and present a user with actionable information. U.S. patent application 20180003558 by Goldring et al. entitled "Accessories for Handheld Spectrometer" appears to disclose a protective sheath having a closed end and an open end which receives a handheld spectrometer.

Muthukumar et al. of the University of Nevada have done innovative research in the field of handheld spectroscopic sensors. U.S. patent application 20150302160 by Muthukumar et al. entitled "Method and Apparatus for Monitoring Diet and Activity" discloses a method and apparatus including a camera and spectroscopy module for determining food types and amounts. This technology appears to have become associated with a product branded as MealCheck in 2016.

TellSpec, which raised funds via Indiegogo in 2014, is a handheld device which uses spectroscopy to measure the nutrient composition of food. Their U.S. patent application 20150036138 by Watson et al. entitled "Analyzing and Correlating Spectra, Identifying Samples and Their Ingredients, and Displaying Related Personalized Information" describes obtaining two spectra from the same sample under two different conditions at about the same time for comparison. Further, this application describes how computing correlations between data related to food and ingredient consumption by users and personal log data (and user entered feedback, user interaction data or personal information related to those users) can be used to detect foods to which a user may be allergic.

Fernstrom et al. of the University of Pittsburgh are pioneers in the use of a wearable video camera to monitor food consumption. Their patents and applications include the following. U.S. patent application 20090012433 by Fernstrom et al., "Method, Apparatus and System for Food Intake and Physical Activity Assessment" and U.S. Pat. No. 9,198,621 by Fernstrom et al., "Method, Apparatus and System for Food Intake and Physical Activity Assessment" appear to disclose devices to measure both food intake and physical activity in a subject, including analysis of video data. U.S. patent application 20130267794 by Fernstrom et al. entitled "Method, Apparatus and System for Food Intake and Physical Activity Assessment" appears to disclose devices to record and analyze food intake and physical activity in a subject, including at least two video cameras and analysis of other physiological and/or environmental data.

U.S. patent application 20150148632 by Benaron entitled "Calorie Monitoring Sensor and Method for Cell Phones, Smart Watches, Occupancy Sensors, and Wearables" discloses a sensor for calorie monitoring in mobile devices, wearables, security, illumination, photography, and other devices and systems which uses an optional phosphor-coated broadband white LED to produce broadband light, which is then transmitted along with any ambient light to a target such as the ear, face, or wrist of a living subject. Calorie monitoring systems incorporating the sensor as well as methods are also disclosed. U.S. patent application 20150148636 by Benaron entitled "Ambient Light Method for Cell Phones, Smart Watches, Occupancy Sensors, and Wearables" discloses a sensor for respiratory and metabolic monitoring in mobile devices, wearables, security, illumination, photography, and other devices and systems that uses a broadband ambient light. The sensor can provide identifying features of type or status of a tissue target, such calories used or ingested.

Application WO 2010/070645 by Einav et al. entitled "Method and System for Monitoring Eating Habits" discloses an apparatus for monitoring eating patterns which can include a spectrometer for detecting nutritious properties of a bite of food. U.S. patent application 20140061486 by Bao et al. entitled "Spectrometer Devices" discloses a spectrometer including a plurality of semiconductor nanocrystals which can serve as a personal UV exposure tracking device. Other applications include a smartphone or medical device wherein a semiconductor nanocrystal spectrometer is integrated.

U.S. patent application 20140349257 by Connor entitled "Smart Watch and Food Utensil for Monitoring Food Consumption" discloses a smart food utensil, probe, or dish that collects data concerning the chemical composition of food which the person is prompted to use when an eating event is detected. U.S. patent application 20150168365 by Connor entitled "Caloric Intake Measuring System Using Spectroscopic and 3D Imaging Analysis" discloses a caloric intake measuring system comprising: a spectroscopic sensor that collects data concerning light that is absorbed by or reflected from food, wherein this food is to be consumed by a person, and wherein this data is used to estimate the composition of this food; and an imaging device that takes images of this food from different angles, wherein these images from different angles are used to estimate the quantity of this food. U.S. Pat. No. 8,355,875 by Hyde et al. entitled "Food Content Detector" discloses a utensil for portioning a foodstuff into first and second portions which can include a spectroscopy sensor. U.S. patent application 20160033328 by Walters entitled "Ambient Light Assisted Spectroscopy" appears to disclose a spectroscopic device which uses ambient light as a primary broadband light source, but which may be supplemented with an auxiliary light source. U.S. patent application 20170292908 by Wilk et al. entitled "Spectrometry System Applications" appears to disclose a spectrometer system which can comprise a spectrometer and a remote server.

U.S. patent application 20170323057 by Karvela et al. entitled "Wearable Device" appears to disclose a wearable device comprising a memory storing a database of product codes and associated product recommendations derived from personalized biological information. U.S. patent application 20170336319 by Hruska et al. entitled "Portable Spectrometer" appears to disclose a portable spectrometer device with a tapered light pipe (TLP) for capturing light interacting with a sample at a first focal ratio and for delivering the light at a second focal ratio lower than the first focal ratio. U.S. Pat. No. 9,717,425 by Kiani et al. entitled "Noise Shielding for a Noninvaise [sic] Device" appears to disclose a noninvasive physiological sensor for measuring one or more physiological parameters of a medical patient and can include a bump interposed between a light source and a photodetector.

SUMMARY OF THE INVENTION

This invention can be embodied in a mobile device for food identification and quantification which has both a spectroscopic sensor (e.g. spectrometer) and a camera. This device can be a handheld food scanner, a handheld food probe, a smart food utensil, a removable attachment for a conventional food utensil, a removable component of a smart watch or wrist band, a component of a cell phone, or a removable accessory for a cell phone.

Spectroscopic analysis can provide information on types of nearby food (and the ingredient, nutrients, chemicals, and/or microorganisms in that food). Changes in the spectrum of light which has been reflected by food are analyzed to obtain information on the molecular composition of that food. Spectroscopic analysis can be particularly useful for analyzing non-standardized food (such as food prepared in restaurants or in homes) for which ingredients are not known. Spectroscopic analysis can provide good information about the molecular and/or nutritional composition of food (and some information about type of food), but does not provide good information on food quantity. Pattern recognition analysis of food images can provide general information on food types and information on food quantity. Analysis of food images can provide good information on the quantities of nearby food, and may also provide some information on food type, but does not always provide good information on the specific molecular and/or nutritional composition of that food.

This mobile device has both a spectroscopic sensor and a camera. It can provide good information on both the types and quantities of nearby food (and ingredients, nutrients, chemicals, and/or possibly even microorganisms in that food). Multivariate statistical analysis of data from a spectroscopic sensor and food images from a camera can provide more accurate identification and quantification of food, nutrients, and/or chemicals than is possible with either spectroscopic data or food images alone. Multivariate analysis can further incorporate subjective descriptions of food types and quantities from a person, in addition to data from a spectroscopic sensor and food images from a camera. In an example, a person can provide descriptions of nearby food types and quantities via speech recognition, keypad entry, or touchscreen contact.

In an example, a mobile device for food identification and quantification can further comprise a light pattern projector which projects a pattern of light onto food or onto a surface near the food. This projected light pattern can serve as a fiducial marker to help estimate food size and/or distance. In an example, a mobile device for food identification and quantification can further comprise a distance finder which measures the distance to food by reflecting light, sound, or radio wave energy from the surface of the food. The operation of this distance finder can be linked with the operation of the camera and/or the spectroscopic sensor (e.g. spectrometer).

In an example, a mobile device for food identification and quantification can be wirelessly linked with a wearable device to comprise a system for monitoring and modifying a person's food consumption habits. In an example, a handheld device for food identification and quantification can be wirelessly linked with a smart watch, wrist band, smart ring, ear bud, or smart eyewear to comprise a system for monitoring and modifying a person's food consumption habits.

INTRODUCTION TO THE FIGURES

FIG. 1 shows this device wherein a beam of light from the spectroscopic sensor is directed toward food.

FIG. 2 shows this device wherein a light pattern is projected from the light pattern projector onto food.

FIG. 3 shows this device wherein the camera takes a picture of food.

FIG. 4 shows an enlarged view of the distal end of the arcuate housing.

DETAILED DESCRIPTION OF THE FIGURES

Figure 1:
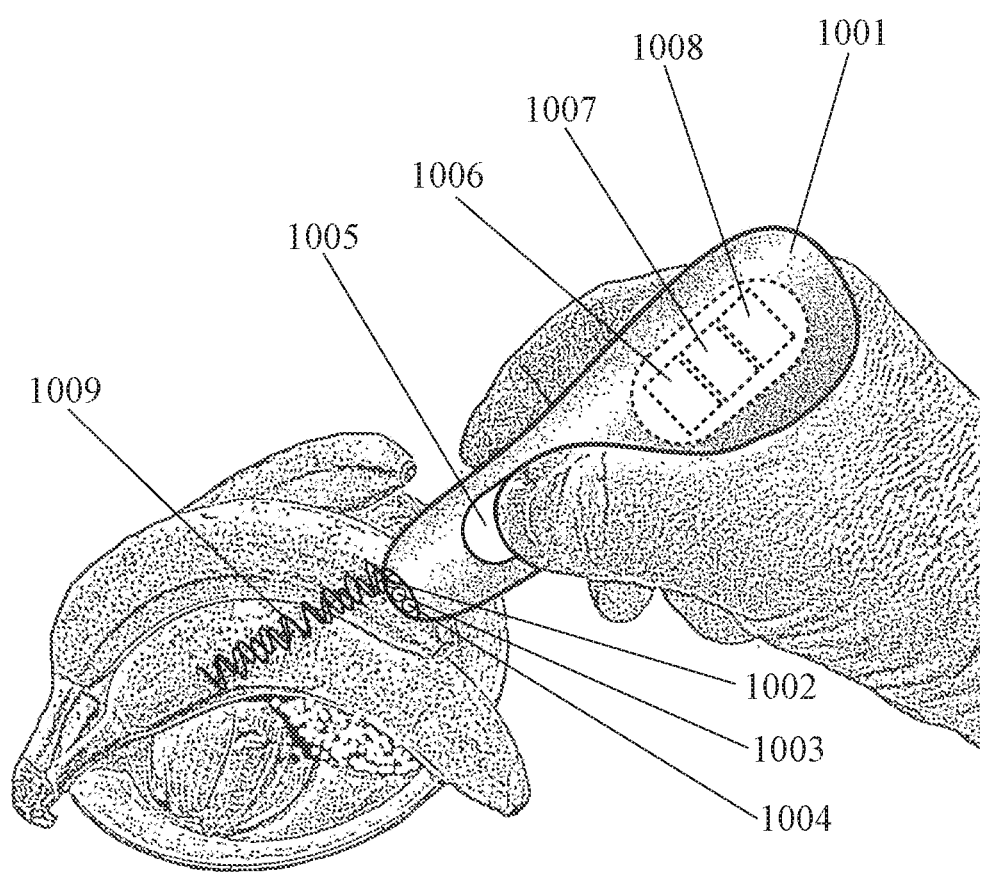
FIGS. 1 through 4 show a mobile device for food identification and quantification comprising a handheld arcuate housing with a spectroscopic sensor, a light pattern projector, and a camera on its distal end.

FIGS. 1 through 7 show some specific examples of how this invention can be embodied. Before discussing FIGS. 1 through 7 specifically, the following introductory section is provided. This introductory section discusses components and variations which can then be applied to FIGS. 1 through 7. This avoids the description redundancy which would result if these components and variations were repeated in the narratives accompanying each of the figures.

Many health problems are caused by poor nutrition. Many people consume unhealthy types of food, unhealthy quantities of food, or both. Although there are complex behavioral reasons for consumption of unhealthy types and quantities of food, better monitoring and awareness concerning the types and quantities of food that a person consumes can help them to improve their nutritional habits. Also, information concerning the types and quantities of food that a person consumes can be part of a system that provides constructive feedback and/or incentives to help the person improve their nutritional intake.

A person can try to monitor the types and quantities of food which they eat without technical assistance. These estimated types and quantities of consumed food can, in turn, be translated into the types and quantities of nutrients (or other chemicals) consumed. However, such unassisted tracking can be subjective. Also, such unassisted tracking can be particularly challenging for non-standardized foods such as those prepared in an ad hoc manner at restaurants or in homes. Who knows what is really in Uncle Bob's Jambalaya? It would be useful to have a convenient mobile device which can help people to identify the types and quantities of nearby food, the types and quantities of nutrients or other chemicals in that food, the presence of microorganisms, or a combination thereof. That is the purpose of this invention.

One technology for analyzing the types of nearby food (and the nutrients, chemicals, and/or microorganisms in that food) is spectroscopic analysis of food. In spectroscopic analysis of food, changes in the spectrum of light which has been reflected by food are analyzed to obtain information on the molecular composition of that food. Spectroscopic analysis can be particularly useful for analyzing non-standardized food (such as food prepared in restaurants or in homes) for which ingredients and/or molecular composition are not well known. Spectroscopic analysis can provide good information about the molecular and/or nutritional composition of food (and some information about type of food), but does not provide good information on food quantity. One technology for analyzing food quantity is pattern recognition analysis of food images. Analysis of food images can provide good information on the quantities of nearby food, and may also provide some information on food type, but does not always provide good information on the specific molecular and/or nutritional composition of that food.

A device which combines both spectroscopic analysis and image analysis can provide good information on both the types and quantities of nearby food (and nutrients, chemicals, and/or possibly even microorganisms in that food). A device with both a spectroscopic sensor (e.g. spectrometer) for spectroscopic analysis of food composition and a camera for pattern recognition of food quantities and general food types can provide good information on both the types and quantities of nearby food, nutrients, and chemicals. Multivariate statistical analysis of data from a spectroscopic sensor and food images from a camera can provide more accurate identification and quantification of food, nutrients, and/or chemicals than is possible with either spectroscopic data or food images alone.

Multivariate analysis can further incorporate subjective descriptions of food types and quantities from a person, in addition to data from a spectroscopic sensor and food images from a camera. In an example, a method for identifying the types and quantities of nearby food (or the ingredients, nutrients, and/or chemicals therein) can comprise: receiving descriptions of nearby food types and quantities from a person; receiving data from spectroscopic sensor analysis of the food; receiving data from pattern analysis of camera images of the food; and performing multivariate analysis on the descriptions from the person, spectroscopic data, and image data in order to identify types and quantities of the food (or the ingredients, nutrients, and/or chemicals therein). In an example, the person can provide descriptions of nearby food types and quantities via speech recognition, keypad entry, or touchscreen contact.

In an example, a mobile device for food identification and quantification can be a handheld device with both a spectroscopic sensor (e.g. spectrometer) to scan food and a camera to record images of food. In an example, a mobile device for food identification and quantification can be embodied in a type of handheld device which is selected from the group consisting of: a handheld food scanner and/or probe; a smart food utensil; a removable attachment for a conventional food utensil; a removable component of a smart watch or wrist band; and a component of a cell phone and/or removable accessory for a cell phone.

In an example, a spectroscopic sensor (e.g. spectrometer) can collect data concerning changes in the spectrum of light that has been reflected from the surface of nearby food and a camera can record images of that food. In an example, data from the spectroscopic sensor and food images from the camera can be jointly analyzed using multivariate analysis to identify the types and quantities of nearby food. In an example, data from the spectroscopic sensor and food images from the camera can be jointly analyzed using multivariate analysis to identify the nutritional and/or general chemical composition of that food. In an example, observed changes in the quantities of different types of nearby food (e.g. from food images at different times) can be analyzed to estimate food consumption by a person.

In an example, a type of food, ingredient, and/or nutrient can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, a series of scans of different food layers, at different times as a person eats the food, can provide a more complete picture of the molecular composition of that food than a single scan of the outer surface of the food before a person starts to eat it. In an example, a mobile device for food identification and quantification can comprise a food probe which is inserted into food to take spectroscopic scans of multiple layers of food. In an example, a food probe can have a transparent housing which is inserted into food and a spectroscopic sensor with one or more moving parts (such as a moving mirror or lens) which scans from different positions along the length of the food probe to scan the molecular composition of different layers of the food. In an example, a food probe which is inserted into food can comprise a longitudinally-moving (e.g. sliding) spectroscopic scanner. In an example, a food probe which is inserted into food can comprise a rotating spectroscopic scanner.

In an example, a mobile device for food identification and quantification can further comprise a light pattern projector which projects a pattern of light onto food or onto a surface near the food. A projected light pattern can serve as a fiducial marker to help estimate food size and/or distance. In an example, the operation of a light pattern projector can be linked with the operation of a camera. In an example, analysis of food images which include a light-projected fiducial marker can help to estimate food volume and quantity. In an example, the operation of a light pattern projector can be linked with the operation of a spectroscopic sensor (e.g. spectrometer). In an example, a projected light pattern can guide a person as to where they should place a spectroscopic sensor to take food scans. In another example, a projected light pattern can be used to record the locations where a spectroscopic sensor was placed for food scans.

In an example, a mobile device for food identification and quantification can further comprise a distance finder which measures the distance to food by reflecting light, sound, or radio wave energy from the surface of food. In an example, the operation of a distance finder can be linked with the operation of a camera and/or the operation of a spectroscopic sensor (e.g. spectrometer). In an example, a camera and/or spectroscopic sensor can be automatically triggered to record images or make scans, respectively, within a selected distance range.

In an example, a mobile device for food identification and quantification can be wirelessly linked with a wearable device to comprise a more-complete system for monitoring and modifying a person's food consumption habits. In an example, a mobile device can be part of a system for food identification and quantification which further comprises a wearable device which is worn by a person. In an example, a handheld device for food identification and quantification can be wirelessly linked with a smart watch, wrist band, smart ring, ear bud, or smart eyewear to comprise a system for monitoring and modifying a person's food consumption habits.

In an example, a person can be prompted to use a mobile device when a wearable device worn by that person detects that that person is starting to eat (if that person has not already used the mobile device). In an example, a person can be prompted (e.g. by vibration, sound, or light) to use a mobile device when a wearable device worn that that person detects that the person is eating (e.g. based on eating-related body sounds or motions). In an example, a person can be prompted to use a mobile device to make spectroscopic scans of food and record images of food when a wearable device worn by that person detects that the person is eating.

In an example, a wearable device (with which this mobile device is wirelessly linked) can detect that a person is eating using one or more sensors selected from the group consisting of: accelerometer, inclinometer, motion sensor, sound sensor, smell sensor, blood pressure sensor, heart rate sensor, EEG sensor, ECG sensor, EMG sensor, electrochemical sensor, gastric activity sensor, GPS sensor, location sensor, image sensor, optical sensor, piezoelectric sensor, respiration sensor, strain gauge, electrogoniometer, chewing sensor, swallow sensor, temperature sensor, and pressure sensor.

In an example, a wearable device (with which this mobile device is wirelessly linked) can detect that a person is eating based on one or more biometric indicators selected from the group consisting of: acceleration, inclination, twisting, or rolling of the person's hand, wrist, or arm; acceleration or inclination of the person's lower arm or upper arm; bending of the person's shoulder, elbow, wrist, or finger joints; movement of the person's jaw, such as bending of the jaw joint; smells suggesting food that are detected by an artificial olfactory sensor; detection of chewing, swallowing, or other eating sounds by one or more microphones; electromagnetic waves from the person's stomach, heart, brain, or other organs; GPS or other location-based indications that a person is in an eating establishment (such as a restaurant) or food source location (such as a kitchen).

In an example, a person can be prompted to take spectroscopic scans at selected locations on food based on the analysis of food images taken by a camera. In an example, food images can be analyzed to identify portions of food of different types on a plate. In an example, a person can be prompted to take spectroscopic scans at different locations associated with portions of food of different types. In an example, suggested locations for these spectroscopic scans can be communicated from the device to the person by a light pattern which is projected onto food at these different locations. In an example, the results of spectroscopic scans of food at a plurality of selected locations on the food can be linked to different types of food in a meal in a food image. In an example, a person can take a scan at a selected location on food and then take a picture of the food with that location highlighted by a light pattern pointed toward that location. These are some of the ways in which the operations of a spectroscopic sensor and a camera can be integrated for superior identification and quantification of nearby food.

In an example, a mobile device for food identification and quantification can be operationally linked with augmented reality eyewear. In an example, augmented reality eyewear can display a virtual pointer at different locations (e.g. different portions or types of food) in a meal to direct where a person should place the spectroscopic sensor (e.g. spectrometer) to take scans of the food. In an example, augmented reality eyewear can track (using gesture recognition) where a person moves a spectroscopic sensor for food scans and link scan results from those locations with different portions or types of food identified by image analysis. In an example, the results of food identification and quantification from a mobile device can be displayed in a person's field of view using augmented reality eyewear. In an example, a mobile handheld device for food identification and quantification and augmented reality eyewear can together comprise a system for monitoring and modifying a person's nutritional intake.

In an example, a mobile device for food identification and quantification can further comprise a microphone and speech recognition capability. In an example, speech recognition capability can enable a person to provide verbal descriptions or estimations of food types and quantities. These descriptions or estimations can be factored into multivariate analysis along with data from the spectroscopic sensor (e.g. spectrometer) and images from the camera in order to better identify the types and quantities of nearby food. In an example, identification of food types and quantities can occur, in an iterative and/or Bayesian manner, with sequential refinement from additional input from the person and the device, or vice versa, until a desired (predicted) level of measurement accuracy is achieved. In an example, a data processor can start with the descriptions of food types and estimations of food quantities provided by the person and then refine them, in a Bayesian manner, based on the results of spectroscopic analysis and food image analysis.

In an example, a mobile device for food identification and quantification can include a handheld housing with a distal end which is pointed toward food. In an example, the distal end of this housing can be concave. In an example, food-facing portions of a spectroscopic sensor (e.g. spectrometer), camera, light projector, and/or distance finder can be located near the center of a distal concavity in order to protect them from direct contact with viscous food which could otherwise smear on them and hinder their operation. In an example, the distal end of this housing can have a recessed area. In an example, food-facing portions of a spectroscopic sensor, camera, light projector, and/or distance finder can be located within this recessed area in order to protect them from direct contact with viscous food which could otherwise smear on them and hinder their operation.

In an example, a mobile device for food identification and quantification can have a housing with an annular portion or protrusion on its distal end which keeps a spectroscopic sensor (e.g. spectrometer), camera, light projector, and/or distance finder from direct contact with viscous food. In an example, a mobile device for food identification and quantification can have an automated lid or cover on its distal end, wherein this lid or cover automatically closes to keep a spectroscopic sensor, camera, light projector, and/or distance finder from direct contact with viscous food when a device is too close to the food surface. In an example, such a lid or cover automatically opens when a device is a safe distance from the food surface. In an example, an automated lid or cover can be transparent. In an example, an automated lid or cover can be easily cleaned.

In an example, a mobile device for food identification and quantification can comprise: (A) an arcuate housing which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; (B) a spectroscopic sensor (e.g. spectrometer), wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; (C) a light pattern projector, wherein the light pattern projector further comprises at least one second energy emitter, wherein the at least one second energy emitter projects a pattern of light from the distal half of the housing onto the food or within 12" of the food, and wherein this pattern of light is used to help measure the quantity of food and/or the distance to the food; and (D) at least one camera on the distal half of the housing, wherein the camera creates images of the food and the projected pattern of light, and wherein the images of the food are analyzed in order to help identify the type of food and/or measure the quantity of food.

In an example, a mobile device for food identification and quantification can comprise: (A) an arcuate housing which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; (B) a spectroscopic sensor (e.g. spectrometer), wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; (C) a distance finder, wherein the distance finder further comprises a second energy emitter and a second energy receiver, wherein the second energy emitter sends sound, light, or other electromagnetic energy from the distal half of the housing toward food, wherein the second energy receiver receives some of the energy sent by the second energy emitter after this energy has been reflected by the food, and wherein the angle, timing, or frequency of the reflected energy is used to measure the distance to the food; and (D) at least one camera on the distal half of the housing, wherein the camera creates images of the food, and wherein the images of the food are analyzed in order to help identify the type of food and/or measure the quantity of food.

In an example, a mobile device for food identification and quantification can comprise: (A) an arcuate housing which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; (B) a spectroscopic sensor (e.g. spectrometer), wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; (C) a distance finder, wherein the distance finder further comprises a second energy emitter and a second energy receiver, wherein the second energy emitter sends sound, light, or other electromagnetic energy from the distal half of the housing toward food, wherein the second energy receiver receives some of the energy sent by the second energy emitter after this energy has been reflected by the food, and wherein the angle, timing, or frequency of the reflected energy is used to measure the distance to the food; (D) a light pattern projector, wherein the light pattern projector further comprises at least one third energy emitter, wherein the at least one third energy emitter projects a pattern of light from the distal half of the housing onto the food or within 12" of the food, and wherein this pattern of light is used to help measure the quantity of food and/or the distance to the food; and (E) at least one camera on the distal half of the housing, wherein the camera creates images of the food and the projected pattern of light, and wherein the images of the food are analyzed in order to help identify the type of food and/or measure the quantity of food.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; (C) a distance finder in the housing, wherein the distance finder further comprises a second energy emitter and a second energy receiver, wherein the second energy emitter sends sound, light, or other electromagnetic energy toward food, wherein the second energy receiver receives some of the energy sent by the second energy emitter after this energy has been reflected by the food, and wherein the angle, timing, or frequency of the reflected energy is used to measure the distance to the food; (D) a light pattern projector in the housing, wherein the light pattern projector further comprises at least one third energy emitter, wherein the at least one third energy emitter projects a pattern of light onto the food or within 12" of the food, and wherein this pattern of light is used to help measure the quantity of food and/or the distance to the food; and (E) at least one camera in the housing, wherein the camera creates images of the food and the projected pattern of light, and wherein the images of the food are analyzed in order to help identify the type of food and/or measure the quantity of food.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; (C) a distance finder in the housing, wherein the distance finder further comprises a second energy emitter and a second energy receiver, wherein the second energy emitter sends sound, light, or other electromagnetic energy toward food, wherein the second energy receiver receives some of the energy sent by the second energy emitter after this energy has been reflected by the food, and wherein the angle, timing, or frequency of the reflected energy is used to measure the distance to the food; and (D) at least one camera in the housing, wherein the camera creates images of the food, and wherein the images of the food are analyzed in order to help identify the type of food and/or measure the quantity of food.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; (C) a light pattern projector in the housing, wherein the light pattern projector further comprises at least one second energy emitter, wherein the at least one second energy emitter projects a pattern of light onto the food or within 12" of the food, and wherein this pattern of light is used to help measure the quantity of food and/or the distance to the food; and (D) at least one camera in the housing, wherein the camera creates images of the food and the projected pattern of light, and wherein the images of the food are analyzed in order to help identify the type of food and/or measure the quantity of food.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; and (C) at least one camera in the housing, wherein the camera creates images of the food, and wherein the images of the food are analyzed in order to help identify the type of food and/or measure the quantity of food.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; (C) a motion sensor in the housing, wherein the motion sensor tracks the number of times a person moves the utensil up to their mouth, and wherein the number of times the person moves the utensil up to their mouth is used to help measure the quantity of food that the person consumers; and (D) at least one camera in the housing, wherein the camera creates images of the food, and wherein the images of the food are analyzed in order to help identify the type of food that the person consumes.

In an example, a mobile device for food identification and quantification can comprise: (A) a housing which is configured to be removably attached to the handle of a food utensil; (B) a spectroscopic sensor (e.g. spectrometer) in the housing, wherein the spectroscopic sensor further comprises at least one first energy emitter and at least one first energy receiver, wherein a first energy emitter sends light beams toward food, wherein a first energy receiver receives some of the light beams after they have been reflected by the food, and wherein changes in the spectrum of the light beams caused by their reflection by the food are analyzed to help identify the type of food; and (C) a motion sensor in the housing, wherein the motion sensor tracks the number of times a person moves the utensil up to their mouth, and wherein the number of times the person moves the utensil up to their mouth is used to help measure the quantity of food that the person consumes.

In an example, a mobile device for food identification and quantification can comprise: (A) a spectroscopic sensor (e.g. spectrometer), wherein the spectroscopic sensor further comprises at least one first energy emitter and at least one first energy receiver, wherein a first energy emitter sends light beams toward food held the by utensil, wherein a first energy receiver receives some of the light beams after they have been reflected by the food, and wherein changes in the spectrum of the light beams caused by their reflection by the food are analyzed to help identify the type of food; (B) at least one camera, wherein the camera creates images of the food, and wherein the images of the food are analyzed in order to help identify the type of food; and (C) a motion sensor, wherein the motion sensor tracks the number of times a person moves the utensil up to their mouth, and wherein the number of times the person moves the utensil up to their mouth is used to help measure the quantity of food that the person consumes.

In an example, a mobile device for food identification and quantification can comprise: (A) a spectroscopic sensor (e.g. spectrometer), wherein the spectroscopic sensor further comprises at least one first energy emitter and at least one first energy receiver, wherein a first energy emitter sends light beams toward food held the by utensil, wherein a first energy receiver receives some of the light beams after they have been reflected by the food, and wherein changes in the spectrum of the light beams caused by their reflection by the food are analyzed to help identify the type of food; and (B) a motion sensor, wherein the motion sensor tracks the number of times a person moves the utensil up to their mouth, and wherein the number of times the person moves the utensil up to their mouth is used to help measure the quantity of food that the person consumes.

In an example, a mobile device for food identification and quantification can comprise: (A) a spectroscopic sensor (e.g. spectrometer), wherein the spectroscopic sensor further comprises at least one first energy emitter and at least one first energy receiver, wherein a first energy emitter sends light beams toward food held the by utensil, wherein a first energy receiver receives some of the light beams after they have been reflected by the food, and wherein changes in the spectrum of the light beams caused by their reflection by the food are analyzed to help identify the type of food; (B) a motion sensor, wherein the motion sensor tracks the number of times a person moves the utensil up to their mouth, and wherein the number of times the person moves the utensil up to their mouth is used to help measure the quantity of food that the person consumers; and (C) a portion of the utensil which can be reversibly detached from the utensil for cleaning.

In an example, a housing of a mobile device for food identification and quantification can be configured to be held between a person's thumb and index finger like a pen, with both its distal and proximal ends extending outward from the person's hand. The distal end can be pointed toward food. In an example, a housing of a mobile device for food identification and quantification can be configured to be held by a person's hand like a computer mouse, with its proximal end fitting into the concavity of the person's palm. The distal end can be pointed toward food. In an example, a housing of a mobile device for food identification and quantification can be configured to be held by a person's hand like a salt shaker, with the end pointed downward toward food designated as its distal end. In an example, a housing of a mobile device for food identification and quantification can be configured to be held by a person's hand like a deck of cards, with the end pointed downward toward food designated as its distal end.

In an example, the housing of a mobile device for food identification and quantification can have a longitudinal axis which is between 1" and 7" in length. In an example, a housing of a mobile device for food identification and quantification can have a middle cross-section which is defined as the cross-sectional slice of the housing in a plane which is perpendicular to the longitudinal axis and which intersects the longitudinal axis half of the way from its proximal end to its distal end. The distal half of the housing is portion of the housing which is distal relative to the middle cross-section. In an example, a housing of a mobile device for food identification and quantification can have a distal-quartile cross-section which is defined as the cross-sectional slice of the housing in a plane which is perpendicular to the longitudinal axis and which intersects the longitudinal axis three-quarters of the way from its proximal end to its distal end. The distal quartile of the housing is portion of the housing which is distal relative to the distal-quartile cross-section.

In an example, a spectroscopic sensor (e.g. spectrometer) can be located in the distal half of the housing of this device. In an example, a distance finder can be located in this distal half. In an example, a light pattern projector can be located in this distal half. In an example, a camera can be located in this distal half. In an example, a spectroscopic sensor, a distance finder, a light pattern projector, and a camera can all be located in this distal half. In an example, this device can include a spectroscopic sensor which is located in a concave distal half of the housing. In an example, this device can include a camera which is located in a concave distal half of the housing. In an example, this device can include a distance finder which is located in a concave distal half of the housing. In an example, this device can include a light pattern projector which is located in a concave distal half of the housing. In an example, a spectroscopic sensor, a camera, a distance finder, and a light pattern projector which are located in a concave distal half of the housing.

In an example, a spectroscopic sensor (e.g. spectrometer) can be located in the distal quartile of the housing of this device. In an example, a distance finder can be located in this distal quartile. In an example, a light pattern projector can be located in this distal quartile. In an example, a camera can be located in this distal quartile. In an example, a spectroscopic sensor, a distance finder, a light pattern projector, and a camera can all be located in this distal quartile. In an example, this device can include a spectroscopic sensor which is located in a concave distal quartile of the housing. In an example, this device can include a camera which is located in a concave distal quartile of the housing. In an example, this device can include a distance finder which is located in a concave distal quartile of the housing. In an example, this device can include a light pattern projector which is located in a concave distal quartile of the housing. In an example, a spectroscopic sensor, a camera, a distance finder, and a light pattern projector which are located in a concave distal quartile of the housing.

In an example, a housing of a mobile device for food identification and quantification can have a lateral cross-section which is perpendicular to its longitudinal axis. In an example, the perimeter of this lateral cross-section can have a shape which is selected from the group consisting of: circular; contact lens shape; egg shape; elliptical; oblong; sinusoidal shape; oval; carlavian curve; peanut shape; pear shape; rounded rectangle; and teardrop shape. In an example, the shape of this perimeter can be asymmetric. In an example, the shape of this perimeter can be concave. In an example, the shape of this perimeter can be convex. In an example, a housing of a mobile device for food identification and quantification can have a longitudinal cross-section which is parallel to its longitudinal axis. In an example, the perimeter of this longitudinal cross-section can have a shape which is selected from the group consisting of: circular; contact lens shape; egg shape; elliptical; oblong; sinusoidal shape; oval; carlavian curve; peanut shape; pear shape; rounded rectangle; and teardrop shape. In an example, the shape of this perimeter can be asymmetric. In an example, the shape of this perimeter can be concave. In an example, the shape of this perimeter can be convex. In an example, a housing of a mobile device for food identification and quantification can be plano-concave or plano-convex.

In an example, a housing of a mobile device for food identification and quantification can have a flat distal end. In an example, one or more of the following components can be located on this flat distal end: a spectroscopic sensor (e.g. spectrometer), a distance finder, a light pattern projector, and a camera. In an example, a housing of a mobile device for food identification and quantification can have a concave distal end. In an example, one or more of the following components can be located on this concave distal end: a spectroscopic sensor, a distance finder, a light pattern pro- jector, and a camera. In an example, having components in the recessed portion of a concave distal end can protect these components from direct contact with viscous food which could otherwise smear onto them. In an example, a housing of a mobile device for food identification and quantification can have a convex distal end. In an example, one or more of the following components can be located on this convex distal end: a spectroscopic sensor, a distance finder, a light pattern projector, and a camera.

In an example, a spectroscopic sensor (e.g. spectrometer), a distance finder, a light pattern projector, or a camera can be located near the center of a distal end of a housing of a mobile device for food identification and quantification. In an example, a spectroscopic sensor, a distance finder, a light pattern projector, or a camera can be located in the center of the recess of a concave distal end of the housing. In an example, a flat or convex distal end can further comprise a ring or other annular member which extends outward from the housing to protect components inside the ring from direct contact with viscous food which could otherwise smear onto them. In an example, the distal end of a housing can have a protrusion which protects sensors from coming into direct contact with viscous food.

In an example, the distal end of a housing can comprise one or more compressible rings, bumps, or ridges which shield spectroscopic sensors (e.g. spectrometers) from con- tamination by direct contact with viscous food. In an example, these rings, bumps, or ridge can also shield those sensors from ambient light which has not been reflected by the food. In an example, a housing of a mobile device for food identification and quantification can further comprise an opaque light-shielding ring, bump, or ridge between a light emitter and a light receiver of a spectroscopic sensor.

In an example, the outer lens of a camera for recording images of food can be located on the distal end of a housing of a mobile device for food identification and quantification. In an example, this distal end can be flat or concave. In an example, the outer lens of a camera for recording food images can be located in the recessed central portion of a concave distal end of this housing in order to protect the lens from being smeared by direct contact with viscous food. In an example, a camera of this device can be configured to automatically take pictures at different distances based on analysis of data from a distance finder. In an example, a person can be prompted to use a camera to take pictures at selected distances based on analysis of data from a distance finder. In an example, a person can be prompted to use a camera to take pictures at different angles based on data from a motion sensor.

In an example, a spectroscopic sensor (e.g. spectrometer) for analyzing food by light reflection can be located on the distal end of a housing of a mobile device for food identi- fication and quantification. In an example, this distal end can be flat or concave. In an example, the spectroscopic sensor can be located in the recessed central portion of a concave distal end of this housing to protect the lens from being smeared by direct contact with viscous food. In an example, a spectroscopic sensor of this device can be configured to automatically scan food at a selected distance based on analysis of data from a distance finder. In an example, a person can be prompted to use a spectroscopic sensor to scan food at a selected distance based on analysis of data from a distance finder. In an example, a person can be prompted to use a spectroscopic sensor to scan food at different locations based on data from a motion sensor.

In an example, a mobile device for food identification and quantification can a spectroscopic sensor (e.g. spectrometer)

with at least one light emitter and at least one light receiver. In an example, a mobile device for food identification and quantification can include one or more spectroscopic sensors which collect data which is analyzed to identify types of nearby food and the relative concentrations of ingredients, nutrients, chemicals, and/or microorganisms in that food. In an example, a spectroscopic sensor can perform one or more types of spectroscopy selected from the group consisting of: absorption spectroscopy; fluorescence spectroscopy; infrared spectroscopy; Raman spectroscopy; reflectance spectroscopy; surface-enhanced Raman spectroscopy; and UV-VIS spectroscopy. In an example, a mobile device for food identification and quantification can include one or more spectroscopic sensors which collect data which is analyzed to identify the nutritional and/or molecular composition of nearby food. In an example, data collected from a spectroscopic sensor can be analyzed to estimate the relative concentrations of protein, fat, sugars, and sodium in nearby food.

In an example, a spectroscopic sensor (e.g. spectrometer) can collect data which is used to analyze the chemical composition of nearby food by measuring the effects of interaction between that food and light energy. In an example, a mobile device for food identification and quantification can include a spectroscopic sensor that collects data concerning changes in the spectrum of light energy which has been reflected by nearby food. In an example, a mobile device for food identification and quantification can include a spectroscopic sensor that collects data concerning changes in the spectrum of light energy which has been transmitted through nearby food. In an example, a mobile device for food identification and quantification can include a spectroscopic sensor that collects data concerning light reflection spectra, absorption spectra, or emission spectra. In an example, a spectroscopic sensor can collect data which is used to analyze the chemical composition of food by measuring the degree of reflection or absorption of light by food at different light wavelengths.

In an example, person can specify a particular substance of interest for which a device should look. In an example, a person may be allergic to a particular type of food, ingredient, or chemical. In an example, a person may have reason to believe that food may be adulterated with a particular substance. In an example, a device may direct in-depth spectroscopic analysis relative to the reflection or absorption spectrum of that particular substance.

In an example, a spectroscopic sensor (e.g. spectrometer) can be located at the distal end of a housing of a mobile device for food identification and quantification. In an example, a spectroscopic sensor can be located in the recessed portion of a concave distal end of this housing to avoid possible direct contact with viscous food surfaces. In an example, a spectroscopic sensor can be located in the tip of a convex distal end of a housing. In an example, the food-facing portion of a spectroscopic sensor can be located in the distal half of this housing. In an example, the food-facing portion of a spectroscopic sensor can be located in the distal quartile of this housing.

In an example, a spectroscopic sensor (e.g. spectrometer) of this device can comprise a light energy emitter which emits near infrared light. In an example, a spectroscopic sensor of this device can comprise a light energy emitter which emits infrared light. In an example, a light energy emitter can emit ultraviolet light. In an example, a light energy emitter can emit light with a wavelength in the range of 400 to 700 nanometers. In an example, a light energy emitter can emit light with a wavelength in the range of 300 to 1200 nanometers. In an example, a light energy receiver can be particularly receptive to near-infrared, infrared, or ultraviolet light. In an example, a mobile device for food identification and quantification can comprise one or more spectroscopic sensors selected from the group consisting of: near-infrared spectroscopic sensor; infrared spectroscopic sensor; white light spectroscopic sensor; and ultraviolet spectroscopic sensor. In an example, one or more light energy emitters can be selected from the group consisting of: white LED, blue LED, red LED, infrared LED, and green LED.

In an example, a mobile device for food identification and quantification can comprise a spectroscopic sensor (e.g. spectrometer) which emits light at different frequencies at different times. In an example, a mobile device for food identification and quantification can comprise a spectroscopic sensor which emits a sequence of light at different frequencies. In an example, a light emitter can emit light with scanning variation in frequencies and/or wavelength. In an example, a light emitter of a spectroscopic sensor can emit light in a sweeping series of frequencies. In an example, a light emitter of a spectroscopic sensor can emit light in a sequentially-varying range of frequencies. In an example, a light emitter of a spectroscopic sensor can emit light with a frequency which changes over time. In an example, a light emitter of a spectroscopic sensor can emit light in a sweeping series of wavelengths. In an example, a light emitter of a spectroscopic sensor can emit light in a sequentially-varying range of wavelengths. In an example, a light emitter of a spectroscopic sensor can emit light with a wavelength which changes over time.

In an example, a spectroscopic sensor (e.g. spectrometer) can comprise a plurality of light emitters which emit light in different wavelength ranges. In an example, a spectroscopic sensor can comprise a plurality of light emitters which emit light at different frequencies and/or wavelengths. In an example, a mobile device for food identification and quantification can comprise a plurality of spectroscopic sensors which sequentially emit light at different frequencies. In an example, a mobile device for food identification and quantification can comprise a plurality of spectroscopic sensors which simultaneously emit light at different frequencies. In an example, the operation of a spectroscopic sensor can include frequency-based modulation.

In an example, a spectroscopic sensor (e.g. spectrometer) can comprise a plurality of light emitters (and/or a device can have a plurality of spectroscopic sensors) which emit light at different times. In an example, a spectroscopic sensor can comprise an array of light emitters which emit light pulses at different times. In an example, a spectroscopic sensor can comprise a linear array of light emitters which emit light pulses at different times. In an example, a spectroscopic sensor can comprise an annular array of light emitters which emit light pulses at different times. In an example, a spectroscopic sensor can comprise a plurality of light emitters which are selectively and sequentially activated. In an example, a plurality of light emitters can be selectively and sequentially activated via time-based multiplexing. In an example, a spectroscopic sensor can operate with time-based multiplexing.

In an example, the timing of light transmitted from a light emitter to a light receiver in a spectroscopic sensor (e.g. spectrometer) can be used to estimate the distance to food as well as collect data concerning the composition of the food. In an example, a spectroscopic sensor can serve a distance finding function in lieu of a separate (dedicated) distance finder component in a mobile device for food identification and quantification. In an example, a mobile device for food identification and quantification can further comprise a speaker which makes a sound or a vibrator which moves when a housing is an optimal first distance from food for spectroscopic analysis. In an example, a mobile device for food identification and quantification can further comprise a speaker which makes a sound or a vibrator which moves when a housing is an optimal second distance from food for food imaging. In an example, the second distance can be greater than the first distance.

In an example, a spectroscopic sensor (e.g. spectrometer) can comprise an array with a plurality of light emitters and a plurality of light receivers. In an example, a spectroscopic sensor can comprise one light emitter and two light receivers. In an example, a spectroscopic sensor can comprise two light emitters and one light receiver. In an example, a spectroscopic sensor can comprise a plurality of light emitters at different locations. In an example, a spectroscopic sensor can comprise a two-dimensional arcuate array with at least one light emitter and at least one light receiver. In an example, a spectroscopic sensor can comprise a three-dimensional array of light emitters and receivers. In an example, a spectroscopic sensor can comprise a plurality of light emitters and receivers in a three-dimensional matrix or grid. In an example, a spectroscopic sensor can comprise a plurality of light emitters which emit light at different angles.

In an example, a spectroscopic sensor (e.g. spectrometer) can comprise a circular or annular array with at least one light emitter and at least one light receiver. In an example, a spectroscopic sensor can comprise a ring of light emitters and receivers. In an example, a spectroscopic sensor can comprise a plurality of light emitters in a ring or circle around a light receiver. In an example, a spectroscopic sensor can comprise at least one light emitter and at least one light receiver in a concentric configuration. In an example, a spectroscopic sensor can comprise a plurality of light emitters in a polygonal configuration around a light receiver. In an example, a spectroscopic sensor can comprise a polygonal array with at least one light emitter and at least one light receiver.

In an example, a spectroscopic sensor (e.g. spectrometer) can further comprise an optical filter. In an example, a spectroscopic sensor can further comprise two-dimensional array of optical filters. In an example, a spectroscopic sensor can further comprise one or more optical filters selected from the group consisting of: optical absorption filter; acousto-optic filter; Bragg filter; cascaded filter; dielectric thin-film filter; Fabry-Perot filter; hybrid filter; and optical interference filter. In an example, a spectroscopic sensor can further comprise one or more optical diffusers. In an example, a spectroscopic sensor can further comprise a two-dimensional lens array. In an example, a spectroscopic sensor can further comprise a three-dimensional lens array. In an example, a spectroscopic sensor can further a digital micromirror device.

In an example, a mobile device for food identification and quantification can further comprise an opaque light-shielding member between a light emitter and a light receiver. In an example, a light-shielding member can reduce the amount of light which is directly transmitted from a light emitter to a light receiver relative to the amount of light from the light emitter which reaches the light receiver after being reflected from nearby food. In an example, a light-shielding member can increase the proportion of light received by a light receiver which has been reflected from the surface of nearby food. In an example, a light-shielding member can be an opaque ring around a light receiver. In an example, this light-shielding member can be an opaque partition between a light emitter and a light receiver. In an example, a light-shielding member can have a longitudinal axis which is substantially parallel to the vector of (collimated or coherent) light beams from a light emitter. In an example, an annular light-shielding member can also help to keep a light emitter or light receiver from direct contact with viscous food.

In an example, a spectroscopic sensor (e.g. spectrometer) can have a cover or lid which automatically closes to prevent the sensor from coming into direct contact with viscous food. In an example, this cover or lid can automatically close when a spectroscopic sensor is within a certain distance from the surface of food, wherein this distance is in the range of 1-100 microns. In an example, this cover or lid can automatically open when a spectroscopic sensor is at least a certain distance from the surface of food, wherein this distance is in the range of 1-100 microns. In an example, this cover or lid can be transparent. In an example, this cover or lid can be easily cleaned if it does come into direct contact with viscous food. In an example, a housing of a mobile device for food identification and quantification can further comprise a movable protrusion on its distal end, wherein this protrusion automatically extends outward from the housing in order to prevent a spectroscopic sensor from coming into direct contact with food when the spectroscopic sensor is within a certain distance from food.

In an example, a mobile device for food identification and quantification can provide an estimate of the degree of certainty with which the type and quantity of nearby food is estimated based on spectroscopic data and image analysis as of a certain time. In an example, this degree of certainty can improve over time with additional scans of the food using a spectroscopic sensor and/or additional imaging of the food using a camera. In an example, there can be a target level of certainty for food identification and quantification. In an example, a person can be prompted to take additional spectroscopic scans and/or take additional pictures of food until this target level of certainty is achieved. In an example, this target level of certainty can be higher when the risk of an error is greater—such as when a device is relied upon to avoid a food to which a person is allergic or to detect a substance in food which could be toxic.

In an example, a method for identifying food types and measuring food quantities can comprise: receiving descriptions of nearby food types and quantities from a person (such as via speech recognition, keypad, or touch screen); receiving data concerning food composition from a spectroscopic sensor (e.g. spectrometer) which is part of a mobile device; receiving data concerning food types and quantities from analysis of images taken by a camera which is part of the mobile device; and using the descriptions from the person, the data from the spectroscopic sensor, and the data from food image analysis in multivariate analysis in order to identify food types and measure food quantities. In an example, this method of multivariate analysis can comprise statistical methods selected from the group consisting of: multivariate linear regression or least squares estimation; principal components analysis; and/or neural network or machine learning. In an example, a device can prompt a person to provide additional descriptions, data from spectroscopic scanning, or food images, in an iterative manner, until a target level of measurement certainty is achieved.

For an example, a person has a plate with fish, carrots, and tomatoes and the person provides their initial subjective description of food types and quantities. The says into a microphone—"fish, one half medium size, carrots, a dozen sticks, tomatoes, one half medium size." The device uses speech recognition software to translate this description into digital information. Then the person uses spectroscopic sensor of the device to scan each of these three types of food on the plate and uses a camera on the device to take multiple images of the food. Then these three types of information are combined in multivariate estimation of food types and quantities. The results of this multivariate estimation can be displayed or spoken by the device. The device says "Tilapia, 8 ounces, carrots, 12 ounces, tomaytoes, 10 ounces." The person responds "you mean tomatoes?" The device says "eh . . . tomaytoes, tomatoes."

In an example, there can be inter-portion food variation in a meal. Inter-portion variation is variation in food characteristics between different portions (e.g. different types) of food in a meal and/or given location. Inter-portion variation can include differences in molecular composition, color, texture, shape, temperature, and location. Different types of food can be identified by inter-portion differences in their molecular composition, color, texture, shape, temperature, and location in a meal. To address inter-portion variation, a person can take spectroscopic scans of different portions of food in a meal. The locations of these scans can be based on the person's evaluation of the number and locations of these different portions. Alternatively, to address inter-portion variation, a device can prompt a person to take spectroscopic scans at different locations and/or of different portions of a meal based on automated analysis of food images.

In an example, there can also be intra-portion food variation in a meal. Intra-portion variation is variation in food characteristics within a portion (e.g. a single type) of food. Inter-portion variation can also include differences in molecular composition, color, texture, shape, temperature, and location. Some foods are non-homogenous. For example, there may be pieces of fruit or nuts at different locations on the outer surface of a portion of food. Different locations on the outer surface of food can have different molecular compositions, colors, textures, shapes, temperatures, or locations. To address intra-portion variation on the outer surface of food, a person can take spectroscopic scans of different locations on the surface of a portion of food based on the person's evaluation different types of ingredients and/or components on that surface.

Foods can also be non-homogenous with respect to inner and outer layers. Inner and outer food layers can have different molecular compositions, colors, textures, shapes, temperatures, or locations. To address intra-portion variation in food layers, a person can take spectroscopic scans of food at different times as they consume food during a meal (e.g. during a defined period of time). To address intra-portion variation in different food layers, a person can take pictures of food at different times as the person consumes the food.

In an example, a camera can automatically take pictures of food at different times during a meal in order to estimate how much of nearby food a person has actually eaten. In an example, after vs. before images can be compared to estimate how much of nearby food a person has actually eaten. In an example, a mobile handheld device can be combined with imaging eyewear into a system for measuring food consumption. The mobile device can include a spectroscopic sensor to identify the molecular composition of food and the imaging eyewear can include a camera to estimate the amount of food which a person actually eats. In an example, changes in the volume of nearby food over time can be analyzed to estimate the quantity of food eaten by a person.

In an example, the degree of uniformity or homogeneity of food can be used to guide a suggested number and/or selected set of locations for spectroscopic scans of nearby food. When food is less-uniform or less-homogenous, then a larger number and wider range of spectroscopic scans can be required for identification and quantification of foods, ingredients, and/or nutrients. When food is more-uniform or more-homogenous, then a smaller number and narrower range of spectroscopic scans can be required for identification and quantification of foods, ingredients, and/or nutrients. In an example, a device can show a person where spectroscopic scans should be made by moving a projected light pattern to different locations on food (like a three-dimensional cursor). In an example, the results of spectroscopic scans at selected locations can be linked to pattern analysis of food images for assessing inter-portion and intra-portion variation in the molecular composition of food.

In an example, a mobile device for food identification and quantification can be wirelessly linked with a cell phone to form a multi-component system for nutritional intake monitoring and modification. In an example, suggested locations on a meal for spectroscopic analysis can be superimposed on a picture of the meal in a cell phone display. In an example, a device can show a person where spectroscopic scans should be made by showing a pointer at different locations on a picture of food. In an example, the results of spectroscopic analysis from selected locations on a meal can be superimposed on a picture of the meal in a cell phone display.

In an example, a mobile device for food identification and quantification can have one or more display lights (e.g. LEDs) whose color changes (in real time) based on the results of a spectroscopic scan of food. In an example, different colors can indicate high concentrations of different types of ingredients, nutrients, and/or chemicals at a particular location based on a particular spectroscopic scan. In an example, different colors can indicate whether a particular portion (type) of food is high in protein, carbohydrates, or fats. In an example, a device can display different colors for different portions (types) of food in a meal. In an example, a mobile device for food identification and quantification can further comprise an LCD display.

In an example, a mobile device for food identification and quantification can have a display screen which shows the results of a spectroscopic scan of food (in real time) in graphic form. In an example, different graphic configurations on a display screen can indicate high concentrations of different types of ingredients, nutrients, and/or chemicals at a particular location based on a particular spectroscopic scan. In an example, different graphic configurations on a display screen can indicate whether a particular portion (type) of food is high in protein, carbohydrates, or fats. In an example, a device can display different graphic configurations for different portions (types) of food in a meal. In an example, a device can be wirelessly linked with a cell phone, wherein these graphic configurations are shown on the display screen of the phone.

In an example, a mobile device for food identification and quantification can have a display screen which shows the results of a spectroscopic scan of food (in real time) via display of icons. In an example, different icons on a display screen can indicate high concentrations of different types of ingredients, nutrients, and/or chemicals at a particular location based on a particular spectroscopic scan. In an example, different icons on a display screen can indicate whether a particular portion (type) of food is high in protein, carbohydrates, or fats. In an example, a device can display different icons for different portions (types) of food in a meal. In an example, a device can be wirelessly linked with a cell phone, wherein these icons are shown on the display screen of the phone.

In an example, a mobile device for food identification and quantification can be wirelessly linked with augmented reality eyewear to form a multi-component system for nutritional intake monitoring and modification. In an example, suggested areas for spectroscopic analysis can be superimposed on a meal in a person's field of view using augmented reality eyewear. In an example, augmented reality eyewear can display one or more virtual pointers at selected locations on a meal to guide a person as to where they should take spectroscopic cans of the meal. For example, augmented reality eyewear may display a virtual pointer on a portion of fish on a plate. The person then uses the handheld device to take a spectroscopic scan of that fish. Then, the augmented reality eyewear may move the virtual point to a portion of carrots on the plate. Then the person takes a scan of the carrots. This continues for each type of food on the plate and/or in the meal. Portion specific spectroscopic information is then combined with food quantity information from analysis of food images to get an overall estimation of types and quantities of foods, ingredients, and/or nutrients. In an example, a mobile device for food identification and quantification can work in combination with augmented reality eyewear, wherein the eyewear identifies locations on food where the person should use the spectroscopic scanner. In an example, augmented reality eyewear can display virtual pointers on food to direct where the person should use a spectroscopic scanner.

In an example, the results of spectroscopic analysis of selected areas in a meal can also be displayed in a person's field of view using augmented reality eyewear. In an example, results of spectroscopic analysis can be displayed in a person's field of vision as a row or column of food types and amounts, ingredient types and amounts, and/or nutrient types and amounts. In an example, such information display can also include icons or images which influence consumption. In an example, augmented reality eyewear can display images which increase or decrease the appeal of selected types of nearby food. In an example, augments reality eyewear can display appetite-reducing images next to unhealthy foods and appetite-enhancing images next to healthy foods. For example, gummi worms may be tempting to a candy lover, but a super-imposed image of actual worms might have the opposite effect. For example, a mug of beer might be appealing, but a super-imposed image of a beer gut might have the opposite effect.

In an example, food images from a camera on a handheld device can be analyzed to suggest selected different locations on food in a meal where a person should take spectroscopic scans. In an example, food images from a camera on smart eyewear, with which a handheld device is wirelessly linked, can be analyzed to suggest selected different locations on food in a meal where a person should take spectroscopic scans. In an example, analysis of food images can be used to direct movement of an automated spectroscopic sensor (e.g. spectrometer). In an example, analysis of food images can be used to change the focal direction of a spectroscopic sensor. In an example, food images from a camera can be analyzed to automatically direct the movement of digital mirror array.

In an example, a projected light pattern can be directed in a sequential manner toward a series of selected locations of a meal where a person should take spectroscopic scans. In an example, a person can move a projected light pattern from one portion (type) of food to another in a meal in order to separately identify each portion (type) of food. In an example, a person can sequentially take spectroscopic scans from one portion (type) to another in the same sequence in which they move the light pattern from one portion (type) to another. This can link each portion of food in a food image with the results of the appropriate spectroscopic scan of that portions. Using these or similar methods, each food portion of a food image can be linked with the results of its corresponding spectroscopic scan.

In an example, the suggested number and dispersion of locations for spectroscopic scans can be based on inter-portion food variability and intra-portion food variability. In an example, food images from a camera can be analyzed to evaluate the uniformity or homogeneity of nearby food. Analysis of food uniformity or homogeneity can include inter-portion variation (e.g. differences in food type between different portions of food in a meal) and intra-portion variation (e.g. differences in ingredients between different parts in a portion of one type of food). A larger number of spectroscopic scans and/or more-dispersed spectroscopic scans can be suggested for a meal with greater inter-portion food variation and/or greater intra-portion food variation.

In an example, a spectroscopic sensor (e.g. spectrometer) can be automatically activated at a given distance range from the surface of food. This distance should be sufficiently close that a high proportion of light hitting the light receiver is reflected from the food, but not so close that the spectroscopic sensor comes into direct contact with viscous food which could smear on the sensor. In an example, a spectroscopic sensor can be automatically activated to emit and receive beams of light at a distance from food which is greater than X and less than Y. In an example, X can be in the range of 1-100 microns. In an example, X can be in the range of 5-500 microns. In an example, a device can further comprise a cover or lid which automatically moves over a spectroscopic sensor at distances less than X to protect the sensor for direct contact with viscous food.

In an example, a spectroscopic sensor can be automatically activated (e.g. turned on) within a given range of distance from food. In an example, a light pattern projector can be automatically activated within a given distance range from food and deactivated outside that distance range. In an example, a light pattern projector can be automatically turned on at a distance range which is optimal for providing a fiducial marker for food images and turned off outside that distance range. In an example, a light pattern projector can be automatically turned off at a distance range which is optimal for spectroscopic analysis so as not to interfere with that spectroscopic analysis).

In an example, a mobile device for food identification and quantification can further comprise one or more actuators which change the focal direction of a spectroscopic sensor (e.g. spectrometer). In an example, a mobile device for food identification and quantification can further comprise one or more actuators which move the focal direction of a spectroscopic sensor back and forth across the surface of nearby food. In an example, a mobile device for food identification and quantification can further comprise one or more actuators which move the focal direction of a spectroscopic sensor in an arcuate pattern over the surface of nearby food.

In an example, a mobile device for food identification and quantification can further comprise one or more actuators which change the focal direction of a digital micromirror array. In an example, a mobile device for food identification and quantification can further comprise one or more actuators which move the focal direction of a digital micromirror array back and forth across the surface of nearby food. In an example, a mobile device for food identification and quantification can further comprise one or more actuators which move the focal direction of a digital micromirror array in an arcuate pattern over the surface of nearby food.

In an example, a mobile device for food identification and quantification can further comprise one or more actuators which change the focal direction of a camera. In an example, a mobile device for food identification and quantification can further comprise one or more actuators which move the focal direction of a camera back and forth across the surface of nearby food. In an example, a mobile device for food identification and quantification can further comprise one or more actuators which move the focal direction of a camera in an arcuate pattern over the surface of nearby food.

In an example, a spectroscopic sensor (e.g. spectrometer), a camera, or a light pattern projector of a mobile device can estimate the distance from the device to nearby food. Alternatively, a mobile device for food identification and quantification can have a dedicated distance finder component. In an example, a distance finder can be different than, distinct from, and/or in addition to a spectroscopic sensor, a camera, and a light pattern projector. In an example, a distance finder can comprise an light emitter and a light receiver. In an example, the timing and/or angle of light transmitted from the light emitter to the light receiver in the spectroscopic sensor can be used to calculate the distance to food. In an example, a distance finder can measure the distance from a device to nearby food by measuring the angle of beams of light which are reflected by food. In an example, a distance finder measure distance to food by measuring the timing of beams of light which are reflected by food. In an example, a distance finder measure distance to food by measuring the frequency of beams of light which are reflected by food.

In an example, a distance finder can comprise an infrared light emitter and an infrared light receiver. In an example, a mobile device can have an infrared-based distance finder. In an example, a distance finder can be based on reflection of infrared light from the surface of nearby food. In an example, a mobile device for food identification and quantification can comprise an infrared light distance finder. The timing, angle, and/or spectrum of infrared light reflected from food can be used to estimate the distance from the device to nearby food. In an example, a distance finder can comprise a coherent light emitter and receiver. In an example, a light emitter can be a laser.

In an example, a mobile device for food identification and quantification can include a sound-based distance finder. In an example, the timing, frequency, or angle of sound waves reflected from nearby food can be used to estimate the distance from a device to that food. In an example, this distance finder can further comprise an ultrasonic energy emitter and an ultrasonic energy receiver. In an example, a distance finder can estimate the distance to nearby food by measuring the timing of sound pluses which are reflected by that food. In an example, a distance finder can estimate the distance to nearby food by measuring the frequency of sound pluses which are reflected by that food. In an example, a distance finder can estimate the distance to nearby food by measuring the angle of sound pluses which are reflected by that food. In an example, a distance finder can be based on sonar.

In an example, a mobile device for food identification and quantification can include a radio wave distance finder. In an example, the timing, frequency, or angle of radio waves reflected from nearby food can be used to estimate the distance from a device to that food. In an example, a distance finder can estimate the distance to nearby food by measuring the timing of radio waves which are reflected by that food. In an example, a distance finder can estimate the distance to nearby food by measuring the frequency of radio waves which are reflected by that food. In an example, a distance finder can estimate the distance to nearby food by measuring the angle of radio waves which are reflected by that food. In an example, a distance finder can be based on radar.

In an example, a spectroscopic sensor (e.g. spectrometer) can be automatically activated at a given distance range from the surface of food. In an example, the distance range can be close enough that a high proportion of light entering the light receiver has been reflected from the surface of nearby food, but not so close that food smears onto the light receiver. In an example, a spectroscopic sensor can be automatically activated to emit and receive beams of light at a distance from food which is greater than X and less than Y. In an example, X can be between 1 and 200 microns, while Y can be between 5 and 500 microns. In an example, X can be between $1/10$th of an inch and 1 inch, while Y can be between $1/4$ of an inch and 3 inches. In an example, this device can have an automatic lid or cover which automatically covers a spectroscopic sensor when the distance from food is less than X or greater than Y. This automatic lid or cover can protect the spectroscopic sensor from being smeared with food and from being scratched when not in use.

In an example, a distance finder can be located in the distal quartile of a housing of a mobile device for food identification and quantification. In an example, a distance finder can be located in the distal half of such a housing. In an example, a housing of a mobile device for food identification and quantification can have a concave distal end wherein a distance finder is located. Alternatively, a housing can have a convex distal end on which a distance finder is located. Alternatively, a housing can have a flat distal end on which a distance finder is located.

In an example, a light pattern projector can turn on automatically when a device is within a given distance range from food and can turn off automatically when the device is outside that range. In an example, the light pattern projector can automatically turn on at a distance range which is good for taking camera images of food so as to provide a projected fiducial marker for food images. However, the light pattern projector and can automatically turn off at a distance range which is good for spectroscopic analysis of food so as not to interfere with spectroscopic analysis. In an example, a light pattern projector can automatically turn on within a given distance range from food, wherein this range distance is between X and Y. In an example, X can be between 2" and 12", while Y can be between 6" and 36".

In an example, a camera can record images automatically when a device is within a given distance range from food and can stop recording images automatically when the device is outside that range. In an example, a camera can automatically record images within a given distance range from food, wherein this range distance is between X and Y. In an example, X can be between 2" and 12", while Y can be between 6" and 36". In an example, a camera can automatically take pictures at different angles based on information from a motion sensor. In an example, a camera can automatically take pictures at different locations based on information from a motion sensor. In an example, this device can have an automatic lid or cover which automatically covers a camera when the distance from food is less than X or greater than Y. This automatic lid or cover can protect the camera from being smeared with food and from being scratched when not in use.

In an example, a mobile device for food identification and quantification can include a light pattern projector which projects a pattern of light onto nearby food and/or onto a surface near the food. In an example, this projected light pattern can serve as a fiducial marker which helps to estimate food scale, size, shape, volume, and/or quantity. In an example, this projected light pattern can be part of food images, wherein it functions as a fiducial marker in pattern analysis which helps to estimate food scale, size, shape, volume, and/or quantity. In an example, this projected light pattern can help to direct locations where a person should take spectroscopic scans of the food. In an example, this projected light pattern can help to link different locations on a food image with the results of different spectroscopic scans at those locations.

In an example, a light pattern projector can be located in the distal quartile of a housing of a mobile device for food identification and quantification. In an example, a light pattern projector can be located in the distal half of such a housing. In an example, a light pattern projector can be located in a concave distal end of such a housing. In an example, a light pattern projector can be located on a flat distal end of such a housing. In an example, a light pattern projector can be located on a convex distal end of such a housing.

In an example, a light pattern projector can comprise one or more LEDs. In an example, a light pattern projector can comprise one or more lasers. In an example, the light pattern projector can project coherent light. In an example, a light pattern projector can project a pattern of coherent light onto food. In an example, a light pattern projector can project a pattern of coherent light onto a surface within 12" of food. In an example, a mobile device for food identification and quantification can comprise a laser which projects coherent light beams onto nearby food (or on a surface near the food), wherein these light beams comprise a virtual fiducial marker which helps to measure the food scale, size, shape, volume, and/or quantity. In an example, a light pattern projector can emit ultraviolet light. In an example, a light pattern projector can emit infrared light. In an example, a light pattern projector can project collimated light.

In an example, a light pattern projector can project patterns of light with different colors onto food. In an example, these different colors can be associated with different types of food, nutrients, chemicals, and/or microorganisms. In an example, a light pattern projector can project different light patterns with different colors indicating different inter-portion boundaries. In an example, the intensity of the light projected by a light pattern projector can be automatically adjusted based on the level of ambient light. In an example, a brighter light pattern can be projected in bright ambient light and a dimmer light pattern can be projected in dim ambient light.

In an example, a light pattern projector can project a circular pattern or ring of light onto food and/or a surface near food. In an example, a circle or ring of light can be a circle or ring of points (or dots) of light. In an example, a circle or ring of light can be a continuous circle or ring of light, such as is produced when a projecting member is rotated. In an example, a circle or ring of light can be a continuous circle or ring of light, such as is produced by a rotating micro-mirror onto which a beam of light is directed. In an example, the angle of the food or the surface on which the food is resting can be estimated by the degree of distortion of the circle or ring. If the food is imaged from directly above the food (or surface), then the projected light pattern is a circle, but if the food is imaged from an angle then it will be an ellipse. The angle of imaging can be determined by the compression of the observed ellipse. In an example, the light pattern projector can project a convex light pattern onto food or surfaces near the food.

In an example, a light pattern projector can project a linear pattern of light onto food and/or a surface near food. In an example, a light pattern projector can project a polygonal light pattern onto food and/or a surface near food. In an example, a light pattern projector can project an array of three points of light onto food or a surface near the food. In an example, a light pattern projector can project a triangular light pattern onto food or a surface near food. In an example, a light pattern projector can project a matrix or grid of light onto food or a surface near food. In an example, a light pattern projector can project a matrix or grid of points (or dots) of light onto food or a surface near food. In an example, a light pattern projector can project an orthogonal light grid onto food. In an example, a light pattern projector can project a two-dimensional array of points of light onto or near food.

In an example, a light pattern which is projected from a projector can be moved across the surface of food by one or more moving micro-mirrors and/or lenses. In an example, an array of moving micromirrors or lenses can move a beam of light across food (or a surface near food) in order to create a pattern or configuration of light. In an example, an array of moving micromirrors or lenses can move a beam of light across food (or a surface near food) in order to create a line of light on the food. In an example, an array of moving micromirrors or lenses can move a beam of light across food (or a surface near food) in order to create a ring or other arcuate configuration of light on the food. In an example, an array of moving micromirrors or lenses can move a beam of light across food (or a surface near food) in order to create a grid or matrix of light on the food.

In an example, a device can automatically identify boundaries between portions (types) of food in a meal and/or on a dish. In an example, a light pattern projector in this device can project light onto the food in a pattern which follows these inter-portion boundaries. In an example, a moving array of micro-mirrors or lenses can direct a beam of light to trace boundaries between portions (types) of food in a meal and/or a dish. Alternatively, a person can manually move a projected beam of light over food in a meal and/or on a disk in order to manually trace out boundaries between different portions (types) of food. In an example, a camera of the device can record these manually traced inter-portion boundaries and use them as an input in the identification of food types and quantification of food quantities. In an example, a mobile device for food identification and quantification can move a light pattern projected by a light pattern projector over food in a meal based on its preliminary automated identification of inter-portion boundaries (between food types), which can then be manually adjusted by the user to further refine them.

In an example, a light pattern project can be turned on automatically within a given distance range from food and can be turned off outside that distance range. In an example, the light pattern can automatically turn on at a distance range which is optimal for taking camera images of food (to provide a fiducial marker for food images) and can automatically turn off at a distance range which is optimal for spectroscopic analysis of food (so as not to interfere with spectroscopic analysis). In an example, a light pattern projector can be automatically activated within a given distance range from food, wherein this range distance is between X and Y, wherein X is between 2" and 12" and wherein Y is between 6" and 36". In an example, a light pattern projector can be linked to a face recognition function (e.g. in the camera) so that it will not project a coherent beam of light onto a person's eyes.

In an example, a light pattern projected by a light pattern projector can be moved to (sequentially) highlight different portions (types) of food in a meal or on a dish, which can then be linked to sequential spectroscopic analysis of the chemical composition of those different portions (types) of food. In an example, food images from a camera can be analyzed to suggest different locations on food where a person should take spectroscopic scans of the food. In an example, food images from a camera can be analyzed to direct the light pattern projector to shine to guide the user where to make spectroscopic scans of the food (e.g. based on inter-portion and intra-portion food variability). In an example, food images from a camera can be analyzed to automatically direct locations on the food where spectroscopic scans are taken.

In an example, a mobile device for food identification and quantification can include a camera which records images (takes pictures) of food. Food includes liquid food (e.g. beverages) as well as solid food. In an example, a mobile device for food identification and quantification can include a camera which records images (e.g. takes pictures) of food which are analyzed to identify food types and estimate food quantities. In an example, a mobile device for food identification and quantification can include a camera which records images (e.g. takes pictures) of food which are analyzed using pattern recognition to identify food types and estimate food quantities. In an example, food images can be wirelessly transmitted to a remote data processor wherein they are analyzed to identify food types and estimate food quantities.

In an example, food characteristics that can be analyzed to identify food types and quantities can be selected from the group consisting of: food color; food texture; food movement; food location in a meal or on a dish; food location with respect to geography (e.g. via GPS); food size; food shape and/or configuration; homogeneous or composite nature of food; food temperature (e.g. via thermal imaging); and food container characteristics. In an example, food images can be analyzed to identify different portions (types) of food in a meal or on a plate. In an example, analysis of food images can include analysis of inter-portion and intra-portion variation in color, texture, movement, location in a meal or on a dish, size, shape, configuration, homogeneous or composite nature, temperature, and container characteristics.

In an example, a camera which is part of mobile device for food identification and quantification can be a video camera. In an example, a camera which is part of mobile device for food identification and quantification can be a still picture camera. In an example, a camera can be configured to record images (e.g. take pictures) of food from multiple angles. In an example, a device can prompt a person to take camera can be configured to record images (e.g. take pictures) of food from multiple angles to construct a three-dimensional digital model of the food. In an example, a device can prompt a person to take camera can be configured to record images (e.g. take pictures) of food from multiple angles to create a volumetric model of the food. In an example, a mobile device for food identification and quantification can automatically record images (e.g. take pictures) of food from different angles as person waves a mobile device over food. In an example, automatic recording of images from different angles can be based on information from a motion sensor. In an example, a mobile device for food identification and quantification can comprise two cameras which create images (e.g. take pictures) of food from different angles, allowing the construction of three-dimensional models of the food.

In an example, food images can be analyzed to identify dishes (such as plates and bowls), beverage holders (such as glasses, cups, and mugs), and/or food utensils (such as forks, spoons, knives, and chop sticks). In an example, identified dishes, beverage holders, or food utensils can be used as an additional input in the identification of food types. Particular types of foods can tend to be located in particular locations or arranged in particular configurations on a plate (e.g. cup of sauce in the middle of a plate). Also, particular types of foods can tend to be served in particular types of dishes or beverage holders (e.g. tea cup or beer mug). Also, particular types of foods can tend to be served accompanied by particular types of utensils (e.g. chop sticks or salad fork). In an example, identified dishes, beverage holders, and/or food utensils can be used as an additional input in the estimation of food size and quantity. For example, forks and spoons tend to have a common size which can serve as a fiducial marker in a food image.

In an example, a camera (e.g. the outside lens or opening thereof) can be located in the distal quartile or distal half of the housing of a mobile device for food identification and quantification. In an example, a camera (e.g. the outside lens or opening thereof) can be located on the distal end of a housing of a mobile device for food identification and quantification. In an example, this distal end can be concave and the camera can be located in the central portion of a concave recess to protect it from being smeared with food. In an example, this distal end can be flat or convex. In an example, two cameras can be located in the distal quartile or distal half of a housing. In an example, two cameras for food imaging can be separated by a distance in the range of ¼" to 3".

In an example, data from analysis of food images from the camera can be combined with data from a spectroscopic sensor (e.g. spectrometer) to identify the types and quantities of nearby food (or the ingredients, nutrients, and/or chemicals therein). In an example, data from analysis of food images from the camera can be combined with data from a spectroscopic sensor (e.g. spectrometer) in multivariate analysis in order to identify the types and quantities of nearby food (or the ingredients, nutrients, and/or chemicals therein).

In an example, a method for identifying the types and quantities of nearby food (or the ingredients, nutrients, and/or chemicals therein) can comprise: receiving descriptions of nearby food types and quantities from a person; receiving data from spectroscopic sensor analysis of the food; receiving data from pattern analysis of camera images of the food; and performing multivariate analysis on the descriptions from the person, spectroscopic data, and image data in order to identify types and quantities of the food (or the ingredients, nutrients, and/or chemicals therein). In an example, the person can provide descriptions of nearby food types and quantities via speech recognition, keypad entry, or touchscreen contact.

In an example, a camera can be triggered to automatically take pictures at selected distances or angles with respect to food. In an example, a camera can be triggered to automatically take pictures at different distances or angles with respect to food as a person waves the device over food. For example, if a person is unsure of the content of a locallybrewed beer, the person can wave their hand (holding the device) slowly over the beer. In an example, the device can respond saying—"These are not the suds you're looking for." In an example, a mobile device for food identification and quantification can include a motion sensor (e.g. comprising an accelerometer and a gyroscope). In an example, a camera can automatically take pictures from selected distances and angles, as informed by the motion sensor. In an example, a camera can take pictures of food within a selected distance range from the food, wherein this range is between X and Y, wherein X is between 2" and 6", and wherein Y is between 6" and 36". In an example, a light pattern projector can also be turned on within this range so that food images include a projected light pattern which serves as a fiducial marker.

In an example, a camera can have an automatic lid and/or cover which closes when it is too close to food. This can protect the camera from being obscured, smeared, or clouded by direct contact with viscous food. In an example, a mobile device for food identification and quantification can have a transparent removable lid or cover on its distal end to protect sensors or cameras from being smeared with food. In an example, this lid or cover can be cleaned in the event of direct contact with food.

In an example, food images from a camera can be analyzed to evaluate the uniformity or homogeneity of food in a meal and/or on a dish. In an example, food images can be analyzed to identify inter-portion food differences (e.g. differences between portions or types of foods in a meal or on a dish) and intra-portion food differences (e.g. non-uniformity of ingredients within a portion of food).

In an example, analysis of inter-portion and intra-portion food variability can inform the number and locations of suggested spectroscopic scans for a meal. In an example, a larger number of spectroscopic scans and/or scans at a wider range of locations can be suggested for meals with greater inter-portion and/or intra-portion variability. In an example, food images from the camera can be analyzed to suggest locations on the food where the user should direct spectroscopic scans of the food. In an example, food images from the camera can be analyzed to automatically direct locations on the food where the user should direct spectroscopic scans of the food. In an example, food images from the camera can be analyzed to direct the light pattern projector to shine to guide the user where to make spectroscopic scans of the food (e.g. based on inter-portion and intra-portion food variability).

In an example, a cell phone (which is wirelessly linked with the mobile device) can display locations on an image of a meal where the device suggests that a person should take spectroscopic scans. In an example, augmented reality eyewear (which is wirelessly linked with the mobile device) can display virtual pointers on a meal in a person's field of vision, indicating where the device suggests that a person should take spectroscopic scans. This can help to identify the molecular compositions of different types of food in a meal.

In an example, food images from a camera on a mobile device for food identification and quantification can be transmitted and/or uploaded to a remote data processor for data processing and/or pattern recognition analysis. In an example, a remote data processor can be a server which is part of "the cloud." In an example, data from a spectroscopic sensor (e.g. spectrometer) and a camera on a mobile device for food identification and quantification can be transmitted and/or uploaded to a remote device (such as a server which is part of the "cloud") for remote analysis and the results of this analysis can be transmitted back to a mobile device for food identification and quantification. In an example, some data processing can be done locally within a data processor in the device and additional data processing can be done in a remote location. In an example, remote processing can include comparison of images with other images in a dataset of images for food identification and/or quantity estimation. In an example, remote processing can convert data on food types and quantities into estimated nutritional and/or chemical quantities using a central dataset with a crosswalk (e.g. conversion table) between food types and nutrients or chemicals. In an example, results from remote processing can be transmitted back to the mobile device (or to a cell phone or to augmented reality eyewear) to inform the person of the results.

In an example, a mobile device for food identification and quantification can have a transparent removable lid or cover on its distal end to protect sensors or cameras from being smeared with food. In an example, this lid or cover can be cleaned after direct contact with food. In an example, a mobile device for food identification and quantification can have an automatic cover and/or lid which closes when it gets too close to food. In an example, the distal end of a housing of a mobile device for food identification and quantification can further comprise a ring surrounding the sensors, wherein this ring makes contact with food and protects sensors from direct contact with food. In an example, a spectroscopic sensor (e.g. spectrometer), distance finder, and/or camera can have an automatic lid and/or cover which closes when the sensor is within a distance of X from the surface of food, wherein X is in the range of 1-100 microns. This lid and/or cover can protect the spectroscopic sensor (e.g. spectrometer), distance finder, and/or camera from being obscured, smeared, or clouded by direct contact with food.

In an example, data from a spectroscopic sensor (e.g. spectrometer) can be combined with data from analysis of food images in multivariate analysis of the types and quantities of food (or ingredients, nutrients, and/or chemicals therein). In an example, a mobile device for food identification and quantification can provide a person with the level of certainty of food type identification and quantity estimation based on available information at a point in time. This level of certainty can change (perhaps even in real time) as additional information is provided, such as from additional food images and/or additional spectroscopic scans. In an example, there can be a target level of certainty and the person can be prompted to provide additional information until the target level of certainty is reached.

In an example, a method for identifying and quantifying nearby food (or ingredients, nutrients, and/or chemicals therein) can comprise: receiving descriptions of nearby food types and quantities from a person (e.g. via speech recognition or keypad entry or touch display entry); receiving data from spectroscopic analysis of the food; receiving data from analysis of images of the food; and conducting multivariate analysis of the descriptions from the person, the spectroscopic data, and the image data in order to identify types and quantities of the nearby food (or ingredients, nutrients, and/or chemicals therein). In an example, this invention can comprise an iterative (or Bayesian) method for identifying and quantifying nearby food (or ingredients, nutrients, and/or chemicals therein) comprising: (1) an initial characterization of food types and quantities from the user; and (2) refinement of this initial characterization based on information from spectroscopic analysis of food composition and pattern recognition analysis of food images.

A wearable device can use biometric information to estimate blood glucose levels, but there is a lag between when food is consumed and when nutrients from this food enter a person's blood stream. In an example, a mobile device for food identification and quantification such as is described in this disclosure can be combined with a wearable biometric device to form a system for predicting and estimating blood glucose levels. This system can use information on current blood glucose levels and also information on food that a person is consuming which can be helpful in predicting changes in glucose levels. In an example, a mobile device for food identification and quantification can be wirelessly linked with a wearable device for non-invasive blood glucose monitoring as part of a system for estimating and/or predicting blood glucose levels. In an example data from the mobile device concerning the types and quantities of food that a person is eating can be used in a multivariate analysis, in combination with biometric information from a wearable device, to estimate and/or predict blood glucose levels more accurately than is possible with either food consumption monitoring or wearable biometric monitoring alone.

In an example, a mobile device with a spectroscopic sensor and a wearable device which measures heart rate, rhythm, and/or rate variability can together comprise an integrated system for food identification and quantification. In an example, when a wearable device detects changes a in person's heart rate, rhythm, and/or rate variation which indicates that the person is eating, then the system can prompt the person to scan food using the spectroscopic sensor. In an example, a mobile device with a camera and a wearable device which measures heart rate, rhythm, and/or rate variability can together comprise a system for food identification and quantification. In an example, when a wearable device detects changes a in person's heart rate, rhythm, and/or rate variation which indicates that the person is eating, then the system can prompt the person to take pictures of the food using the camera.

In an example, a mobile device with a spectroscopic sensor and a wearable device which measures electromagnetic brain activity can together comprise an integrated system for food identification and quantification. In an example, when a wearable device detects changes a in person's electromagnetic brain activity which indicates that the person is eating, then the system can prompt the person to scan food using the spectroscopic sensor. In an example, a mobile device with a camera and a wearable device which measures electromagnetic brain activity can together comprise a system for food identification and quantification. In an example, when a wearable device detects changes a in person's electromagnetic brain activity which indicates that the person is eating, then the system can prompt the person to take pictures of the food using the camera.

In an example, a mobile device for food identification and quantification can comprise a hand-held food probe which collects data to analyze the chemical composition of nearby food. In an example, a mobile food probe can be inserted into food in order to take spectroscopic scans at different depths of the food. In an example, a mobile food probe can be inserted into food in order to take spectroscopic scans of different food layers. In an example, a mobile food probe can comprise a transparent housing within which is a moving spectroscopic scanner. In an example, a mobile food probe can comprise a transparent housing with a longitudinal axis, wherein a spectroscopic scanner is moved inward and/or outward along this longitudinal axis to analyze the molecular composition of food at different food layers and/or depths. In an example, a mobile food probe can comprise a transparent housing with a longitudinal axis, wherein a spectroscopic scanner is rotated around this longitudinal axis to analyze the molecular composition of food at different circumferential locations relative to the food probe. In an example, a mobile food probe which is inserted into food can have a mirror or lens which is moved along its longitudinal axis to direct a beam of light to different food layers or depths, thereby enabling analysis of the molecular composition of food at different food layers or depths.

In an example, a mobile device for food identification and quantification can be embodied in a smart food utensil. In an example, mobile device for food identification and quantification can be a smart fork, spoon, knife, or chop stick with a chemical composition sensor. In an example, mobile device for food identification and quantification can be a smart fork, spoon, knife, or chop stick which has a camera, spectroscopic sensor, and motion sensor as part of its handle. In an example, a mobile device for food identification and quantification can be embodied in a smart beverage container. In an example, a smart beverage container (e.g. a "Smug Mug") can comprise a camera, spectroscopic sensor, and motion sensor.

In an example, a mobile device for food identification and quantification can be a smart fork which has a spectroscopic sensor, a camera, and a motion sensor. In an example, the camera can take pictures of nearby food and/or food on the fork's tines. In an example, the spectroscopic sensor can scan food on the fork's tines. In an example, the motion sensor can track how many times the fork is raised up to a person's mouth. Information from the camera, spectroscopic sensor, and motion sensor can be jointly analyzed to identify and quantify food which the person eats (and associated ingredients, nutrients, and/or chemicals).

In an example, a mobile device for food identification and quantification can be a smart spoon which has a spectroscopic sensor, a camera, and a motion sensor. In an example, the camera can take pictures of nearby food and/or food in the spoon's concavity. In an example, the spectroscopic sensor can scan food on the spoon's concavity. In an example, the motion sensor can track how many times the spoon is raised up to a person's mouth. Information from the camera, spectroscopic sensor, and motion sensor can be jointly analyzed to identify and quantify food which the person eats (and associated ingredients, nutrients, and/or chemicals).

In an example, a mobile device for food identification and quantification can be removably attached to the handle an ordinary food utensil such as a fork, spoon, knife, or chop stick. In an example, such a mobile device can be removably attached to the handle of a fork, spoon, knife, or chop stick by a clip, clasp, clamp, snap, magnet, hook, hook and eye material, elastic band, compression band, buckle or latch, pin, adhesive, or rotating threaded mechanism (such as a screw or nut). In an example, a mobile device for food identification and quantification can be removably attached to a beverage container such as a glass, mug, cup, or bottle.

In an example, a mobile device for food identification and quantification can be part of a system which further comprises a wearable device which detects when a person is eating. In an example, such a system can prompt a person (e.g. via vibration, voice, sound, or light) to use the mobile device to scan food and/or take pictures of food when the person is eating. In an example, a person can be prompted to use a mobile device for food identification and quantification when a wearable device detects that they are eating. In an example, eating can be detected by a person swallowing a selected number of times in a period of time, by a pattern of chewing, and/or by a pattern of repeated hand motions. In an example, a wearable device can be selected from the group consisting of: smart watch; wrist band; necklace and/or pendant; ear bud; and eyewear.

In an example, a mobile device for food identification and quantification can be part of a system which further comprises smart eyewear. In an example, the smart eyewear can take pictures of nearby food. In an example, the smart eyewear can be augmented reality eyewear which superimposes virtual text and/or images over nearby food in a person's field of vision. In an example, augmented reality eyewear can display information on food content and/or type based on data collected from different locations by the spectroscopic sensor (e.g. spectrometer). In an example, augmented reality eyewear can display locations (e.g. using a virtual pointer) on nearby food where a person should use a spectroscopic scanner. In an example, augmented reality eyewear can superimpose unappetizing images or negative icons in a person's field of vision on (or near) food which is determined to be unhealthy based on spectroscopic analysis. In an example, augmented reality eyewear can superimpose appetizing images or positive icons in a person's field of vision on (or near) food which is determined to be healthy based on spectroscopic analysis.

In an example, a mobile device for food identification and quantification can comprise a speaker through which auditory feedback can be provided to a person. In an example, a mobile device for food identification and quantification can comprise a microphone through which a person can provide oral commands and/or information to the device. In an example, person can point a virtual light pattern (e.g. a laser pointer) over a portion of food and say what they think the food is and how much they think it is. The device can translate this into digital information using speech recognition. The person can also take a spectroscopic scan at that location and the results of that scan can be linked to the person's oral description. The person can also take a picture focused on that location and that picture can be linked to the person's oral description. In an example, person can use their hand to point to a portion of food and this can be interpreted by the device using gesture recognition.

In an example, a mobile device for food identification and quantification can further comprise a speaker. In an example, this speaker can make a sound when the housing is an optimal distance from food for spectroscopic analysis and/or camera imaging. In an example, a mobile device for food identification and quantification can further comprise an actuator and/or vibrator. In an example, this actuator and/or vibrator can vibrate when the housing is an optimal distance from food for spectroscopic analysis and/or camera imaging. In an example, a mobile device for food identification and quantification can further comprise a light. In an example, this light can flash when the housing is an optimal distance from food for spectroscopic analysis and/or camera imaging. In an example, a mobile device for food identification and quantification can further comprise a speaker which makes a sound, a vibrator which vibrates, or a light which flashes when a housing is too close to the food, wherein being too close might smear food on a spectroscopic sensor, camera, or distance finder.

In an example, a mobile device for food identification and quantification can further comprise a motion sensor. In an example, a mobile device for food identification and quantification can further comprise an accelerometer and a gyroscope. In an example, a camera can automatically take pictures of food from selected distances and angles, as informed by data from a motion sensor. In an example, a mobile device for food identification and quantification can further comprise a thermometer or other heat sensor. In an example, thermal data can be used to calibrate analysis of data from a spectroscopic sensor (e.g. spectrometer).

In an example, a mobile device for food identification and quantification can further comprise one or more components selected from the group consisting of: battery; CCD or CMOS; data processor; data receiver; data transmitter; display screen; GPS component; keypad; kinetic energy transducer; LCD display; memory; optical diffuser; power source; speaker; thermal energy transducer; touch screen; and voice recognition interface.

In an example, a mobile device for food identification and quantification can help to identify and quantify one or more types of foods, ingredients, nutrients, and/or chemicals selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In various examples, a mobile device for food identification and quantification can help to identify and quantify one or more types of nutrients and/or chemicals selected from the group consisting of: simple carbohydrates, simple sugars, saturated fat, trans fat, Low Density Lipoprotein (LDL), and salt. In an example, a mobile device can help to identify and quantify simple carbohydrates. In an example, a mobile device can help to identify and quantify simple sugars. In an example, a mobile device can help to identify and quantify saturated fats. In an example, a mobile device can help to identify and quantify trans fats. In an example, a mobile device can help to identify and quantify Low Density Lipoprotein (LDL). In an example, a mobile device can help to identify and quantify sodium.

In various examples, a mobile device for food identification and quantification can help to identify and quantify one or more foods, ingredients, nutrients, and/or chemicals selected from the group consisting of: amino acid or protein (a selected type or general class), carbohydrate (a selected type or general class, such as single carbohydrates or complex carbohydrates), cholesterol (a selected type or class, such as HDL or LDL), dairy products (a selected type or general class), fat (a selected type or general class, such as unsaturated fat, saturated fat, or trans fat), fiber (a selected type or class, such as insoluble fiber or soluble fiber), mineral (a selected type), vitamin (a selected type), nuts (a selected type or general class, such as peanuts), sodium compounds (a selected type or general class), sugar (a selected type or general class, such as glucose), and water. In an example, food can be classified into general categories such as fruits, vegetables, or meat.

In an example, a mobile device for food identification and quantification can help to identify and quantify food that is high in simple carbohydrates. In an example, a mobile device can help to identify and quantify food that is high in simple sugars. In an example, a mobile device can help to identify and quantify food that is high in saturated fats. In an example, a mobile device can help to identify and quantify food that is high in trans fats. In an example, a mobile device can help to identify and quantify food that is high in Low Density Lipoprotein (LDL). In an example, a mobile device can help to identify and quantify food that is high in sodium.

In an example, a mobile device for food identification and quantification can help to identify and quantify food wherein a high proportion of its calories comes from simple carbohydrates. In an example, a mobile device can help to identify and quantify food wherein a high proportion of its calories comes from simple sugars. In an example, a mobile device can help to identify and quantify food wherein a high proportion of its calories comes from saturated fats. In an example, a mobile device can help to identify and quantify food wherein a high proportion of its calories comes from trans fats. In an example, a mobile device can help to identify and quantify food wherein a high proportion of its calories comes from Low Density Lipoprotein (LDL). In an example, a mobile device can help to identify and quantify food wherein a high proportion of its weight or volume is comprised of sodium compounds.

In an example, a mobile device for food identification and quantification can track quantities of selected chemicals in food. In various examples, these chemicals can be selected from the group consisting of carbon, hydrogen, nitrogen, oxygen, phosphorus, and sulfur. In an example, a mobile device for food identification and quantification can selectively detect consumption of one or more types of unhealthy food, wherein unhealthy food is selected from the group consisting of: food that is high in simple carbohydrates; food that is high in simple sugars; food that is high in saturated or trans fat; fried food; food that is high in Low Density Lipoprotein (LDL); and food that is high in sodium.

Many people consume highly-processed foods whose primary ingredients include multiple types of sugar. The total amount of sugar is often obscured or hidden, even from those who read ingredients on labels. Sometimes sugar is disguised as "evaporated cane syrup." Sometimes different types of sugar are labeled as different ingredients (such as "plain sugar," "brown sugar," "maltose", "dextrose," and "evaporated cane syrup") in a single food item. In such cases, "sugar" does not appear as the main ingredient. However, when one adds up all the different types of sugar in different priority places on the ingredient list, then sugar really is the main ingredient. These highly-processed conglomerations of sugar (often including corn syrup, fats, and/or caffeine) often have colorful labels with cheery terms like "100% natural" or "high-energy." However, they are unhealthy when eaten in the quantities to which many Americans have become accustomed. It is no wonder that there is an obesity epidemic. The mobile device for food identification and quantification disclosed herein is not be fooled by deceptive labeling of ingredients.

In a broad range of examples, a mobile device for food identification and quantification can help to identify and quantify one or more types of foods, ingredients, nutrients, and/or chemicals selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a mobile device for food identification and quantification can also identify one or more potential food allergens, toxins, or other substances selected from the group consisting of: ground nuts, tree nuts, dairy products, shell fish, eggs, gluten, pesticides, animal hormones, and antibiotics. In an example, a mobile device for food identification and quantification can analyze food composition to identify one or more types of food whose consumption is prohibited or discouraged for religious, moral, and/or cultural reasons, such as pork or meat products of any kind.

Amounts or quantities of food, ingredients, and nutrients can be measured in terms of volume, mass, or weight. Volume measures how much space the food occupies. Mass measures how much matter the food contains. Weight measures the pull of gravity on the food. The concepts of mass and weight are related, but not identical. Food, ingredient, or nutrient density can also be measured, sometimes as a step toward measuring food mass.

Volume can be expressed in metric units (such as cubic millimeters, cubic centimeters, or liters) or U.S. (historically English) units (such as cubic inches, teaspoons, tablespoons, cups, pints, quarts, gallons, or fluid ounces). Mass (and often weight in colloquial use) can be expressed in metric units (such as milligrams, grams, and kilograms) or U.S. (historically English) units (ounces or pounds). The density of specific ingredients or nutrients within food is sometimes measured in terms of the volume of specific ingredients or nutrients per total food volume or measured in terms of the mass of specific ingredients or nutrients per total food mass.

In an example, the amount of a specific ingredient or nutrient within (a portion of) food can be measured directly by a sensing mechanism. In an example, the amount of a specific ingredient or nutrient within (a portion of) food can be estimated indirectly by measuring the amount of food and then linking this amount of food to amounts of ingredients or nutrients using a database that links specific foods with standard amounts of ingredients or nutrients. In an example, a mobile device for food identification and quantification can identify selected types food, ingredients, and/or nutrients using a database that links common types and amounts of food with common types and amounts of ingredients or nutrients.

In an example, an amount of a selected type of food, ingredient, or nutrient can be expressed as an absolute amount. In an example, an amount of a selected type of food, ingredient, or nutrient can be expressed as a percentage of a standard amount. In an example, an amount of a selected type of food, ingredient, or nutrient can be displayed as a portion of a standard amount such as in a bar chart, pie chart, thermometer graphic, or battery graphic.

In an example, a standard amount can be selected from the group consisting of: daily recommended minimum amount; daily recommended maximum amount or allowance; weekly recommended minimum amount; weekly recommended maximum amount or allowance; target amount to achieve a health goal; and maximum amount or allowance per meal. In an example, a standard amount can be a Reference Daily Intake (RDI) value or a Daily Reference Value.

In an example, the volume of food can be estimated by analyzing one or more pictures of that food. In an example, volume estimation can include the use of a physical or virtual fiducial marker or object of known size for estimating the size of a portion of food. In an example, a physical fiducial marker can be placed in the field of view of an imaging system for use as a point of reference or a measure. In an example, this fiducial marker can be a plate, utensil, or other physical place setting member of known size. In an example, this fiducial marker can be created virtually by the projection of coherent light beams. In an example, a mobile device for food identification and quantification can project (laser) light points onto food and, in conjunction with infrared reflection or focal adjustment, use those points to create a virtual fiducial marker. A fiducial marker may be used in conjunction with a distance-finding mechanism (such as infrared range finder) that determines the distance from the camera and the food.

In an example, volume estimation can include obtaining video images of food or multiple still pictures of food in order to obtain pictures of food from multiple perspectives. In an example, pictures of food from multiple perspectives can be used to create three-dimensional or volumetric models of that food in order to estimate food volume. In an example, such methods can be used prior to food consumption and again after food consumption, in order to estimate the volume of food based on differences in food volume measured. In an example, food volume estimation can be done by analyzing one or more pictures of food before (and after) consumption. In an example, multiple pictures of food from different angles can enable three-dimensional modeling of food volume. In an example, multiple pictures of food at different times (such as before and after consumption) can enable estimation of the amount of proximal food that is actually consumed vs. just being served in proximity to the person.

In a non-imaging example of food volume estimation, a utensil or other apportioning device can be used to divide food into mouthfuls. Then, the number of times that the utensil is used to bring food up to the person's mouth can be tracked. Then, the number of utensil motions is multiplied times the estimated volume of food per mouthful in order to estimate the cumulative volume of food consumed. In an example, the number of hand motions or mouth motions can be used to estimate the quantity of food consumed. In an example, a motion sensor worn on a person's wrist or incorporated into a utensil can measure the number of hand-to-mouth motions. In an example, a motion sensor, sound sensor, or electromagnetic sensor in communication with a person's mouth can measure the number of chewing motions which, in turn, can be used to estimate food volume.

In an example, a mobile device for food identification and quantification can measure the weight or mass of food. In an example, a mobile device for food identification and quantification can be wirelessly linked to a food scale that measures the weight of food. In an example a food scale can measure the weight of food prior to consumption and the weight of unconsumed food remaining after consumption in order to estimate the weight of food consumed based on the difference in pre vs. post consumption measurements. In an example, a food scale can be a stand-alone device. In an example, a food scale can be incorporated into a plate, glass, cup, glass coaster, place mat, or other place setting. In an example a plate can include different sections which separately measure the weights of different foods on the plate. In an example, a food scale embedded into a place setting or smart utensil can automatically transmit data concerning food weight to a computer.

In an example, a food scale can be incorporated into a smart utensil. In an example, a food scale can be incorporated into a utensil rest on which a utensil is placed for each bite or mouthful. In an example, a food scale can be incorporated into a smart utensil which tracks the cumulative weight of cumulative mouthfuls of food during an eating event. In an example, a smart utensil can approximate the weight of mouthfuls of food by measuring the effect of food carried by the utensil on an accelerometer or other inertial sensor. In an example, a smart utensil can incorporate a spring between the food-carrying portion and the hand-held portion of a utensil and food weight can be estimated by measuring distension of the spring as food is brought up to a person's mouth.

In an example, a smart utensil can use an inertial sensor, accelerometer, or strain gauge to estimate the weight of the food-carrying end of utensil at a first time (during an upswing motion as the utensil carries a mouthful of food up to the person's mouth), can use this sensor to estimate the weight of the food-carrying end of the utensil at a second time (during a downswing motion as the person lowers the utensil from their mouth), and can estimate the weight of the mouthful of food by calculating the difference in weight between the first and second times.

In an example, a mobile device for food identification and quantification can measure nutrient density or concentration as part of an automatic food, ingredient, or nutrient identification method. In an example, such nutrient density can be expressed as the average amount of a specific ingredient or nutrient per unit of food weight. In an example, such nutrient density can be expressed as the average amount of a specific ingredient or nutrient per unit of food volume. In an example, food density can be estimated by interacting food with light, sound, or electromagnetic energy and measuring the results of this interaction. Such interaction can include energy absorption or reflection.

In an example, nutrient density can be determined by reading a label on packaging associated with food. In an example, nutrient density can be determined by receipt of wirelessly transmitted information from a grocery store display, electronically-functional restaurant menu, or vending machine. In an example, food density can be estimated by ultrasonic scanning of food. In an example, food density and food volume can be jointly analyzed to estimate food weight or mass. In an example, a mobile device for food identification and quantification can read a bar code (or other digital marking) on food packaging. In an example, for some foods with standardized sizes (such as foods that are manufactured in standard sizes at high volume), food weight can be estimated as part of food identification. In an example, information concerning the weight of food can be linked to nutrient quantities in a computer database in order to estimate cumulative consumption of selected types of nutrients.

In an example, a method for food identification and quantification can comprise monitoring changes in the volume or weight of food at a reachable location near the person. In an example, pictures of food can be taken at multiple times before, during, and after food consumption in order to better estimate the amount of food that the person actually consumes, which can differ from the amount of food served to the person or the amount of food left over after the person eats. In an example, estimates of the amount of food that the person actually consumes can be made by digital image subtraction and/or 3D modeling. In an example, changes in the volume or weight of nearby food can be correlated with hand motions in order to estimate the amount of food that a person actually eats. In an example, a mobile device for food identification and quantification can track the cumulative number of hand-to-mouth motions, number of chewing motions, or number of swallowing motions. In an example, estimation of food consumed can also involve asking the person whether they ate all the food that was served to them.

In an example, a device for food identification and quantification can collect data that enables tracking the cumulative amount of a type of food, ingredient, or nutrient which the person consumes during a period of time (such as an hour, day, week, or month) or during a particular eating event. In an example, the time boundaries of a particular eating event can be defined by a maximum time between chews or mouthfuls during a meal and/or a minimum time between chews or mouthfuls between meals. In an example, the time boundaries of a particular eating event can be defined by Fourier Transformation analysis of the variable frequencies of chewing, swallowing, or biting during meals vs. between meals.

In an example, a device for food identification and quantification can track the cumulative amount of that food, ingredient, or nutrient consumed by the person and provide feedback to the person based on the person's cumulative consumption relative to a target amount. In an example, a mobile device can provide negative feedback when a person exceeds a target amount of cumulative consumption. In an example, a device for food identification and quantification can sound an alarm or provide other real-time feedback to a person when the cumulative consumed amount of a selected type of food, ingredient, or nutrient exceeds an allowable amount (in total, per meal, or per unit of time).

In various examples, a target amount of consumption can be based on one or more factors selected from the group consisting of: the selected type of selected food, ingredient, or nutrient; amount of this type recommended by a health care professional or governmental agency; specificity or breadth of the selected nutrient type; the person's age, gender, and/or weight; the person's diagnosed health conditions; the person's exercise patterns and/or caloric expenditure; the person's physical location; the person's health goals and progress thus far toward achieving them; one or more general health status indicators; magnitude and/or certainty of the effects of past consumption of the selected nutrient on the person's health; the amount and/or duration of the person's consumption of healthy food or nutrients; changes in the person's weight; time of day; day of the week; occurrence of a holiday or other occasion involving special meals; dietary plan created for the person by a health care provider; input from a social network and/or behavioral support group; input from a virtual health coach; health insurance copay and/or health insurance premium; financial payments, constraints, and/or incentives; cost of food; speed or pace of nutrient consumption; and accuracy of a sensor in detecting a selected nutrient.

FIGS. 1 through 7 show some specific examples of how this invention can be embodied, but do not restrict the full generalizability of the final claims. Example and component variations which have been discussed thus far in this disclosure (and also in other disclosures which are linked by priority claim) can be applied where relevant to the examples in FIGS. 1 through 7 but are not repeated in the narratives accompanying these figures in order to reduce duplicative content. We now discuss FIGS. 1 through 7, starting with FIGS. 1 through 4.

FIGS. 1 through 4 show an example of a mobile device for food identification and quantification comprising: an arcuate housing 1001 which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; a spectroscopic sensor 1002, wherein the spectroscopic sensor further comprises at least one first energy emitter and at least one first energy receiver, wherein a first energy emitter sends light beams 1009 from the distal half of the housing toward food, wherein a first energy receiver receives some of the light beams after they have been reflected by the food, and wherein changes in the spectrum of the light beams caused by their reflection by the food are analyzed to help identify the type of food; a light pattern projector 1004, wherein the light pattern projector further comprises at least one second energy emitter, wherein the at least one second energy emitter projects a pattern of light from the distal half of the housing onto the food or within 12" of the food, and wherein this pattern of light is used to help measure the quantity of food and/or the distance to the food; and a camera 1003 on the distal half of the housing, wherein the camera creates images of the food and the projected pattern of light, and wherein the images of the food are analyzed in order to help identify the type of food and/or measure the quantity of food. The device in FIG. 1 further comprises a button 1005, battery 1006, data processor 1007, and data transmitter/receiver 1008. Other components and design variations described in other portions of this disclosure and priority-linked disclosures can also be applied to this figure.

Figure 2:
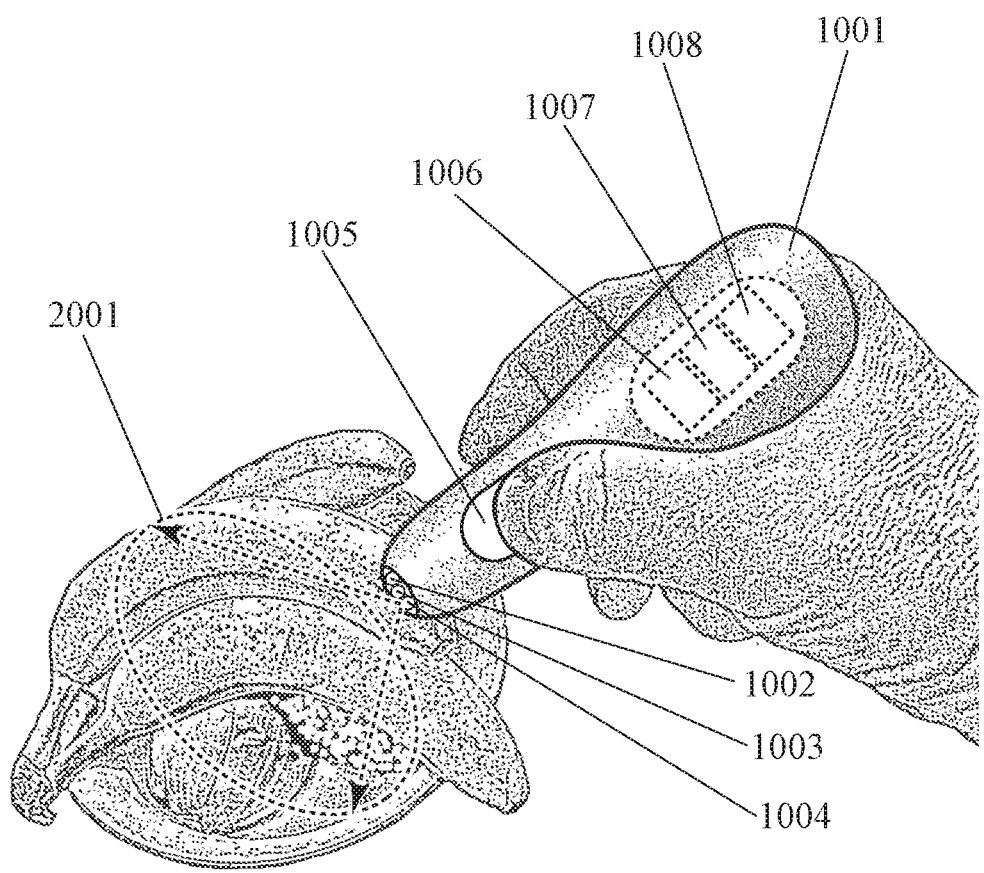
Figure 3:
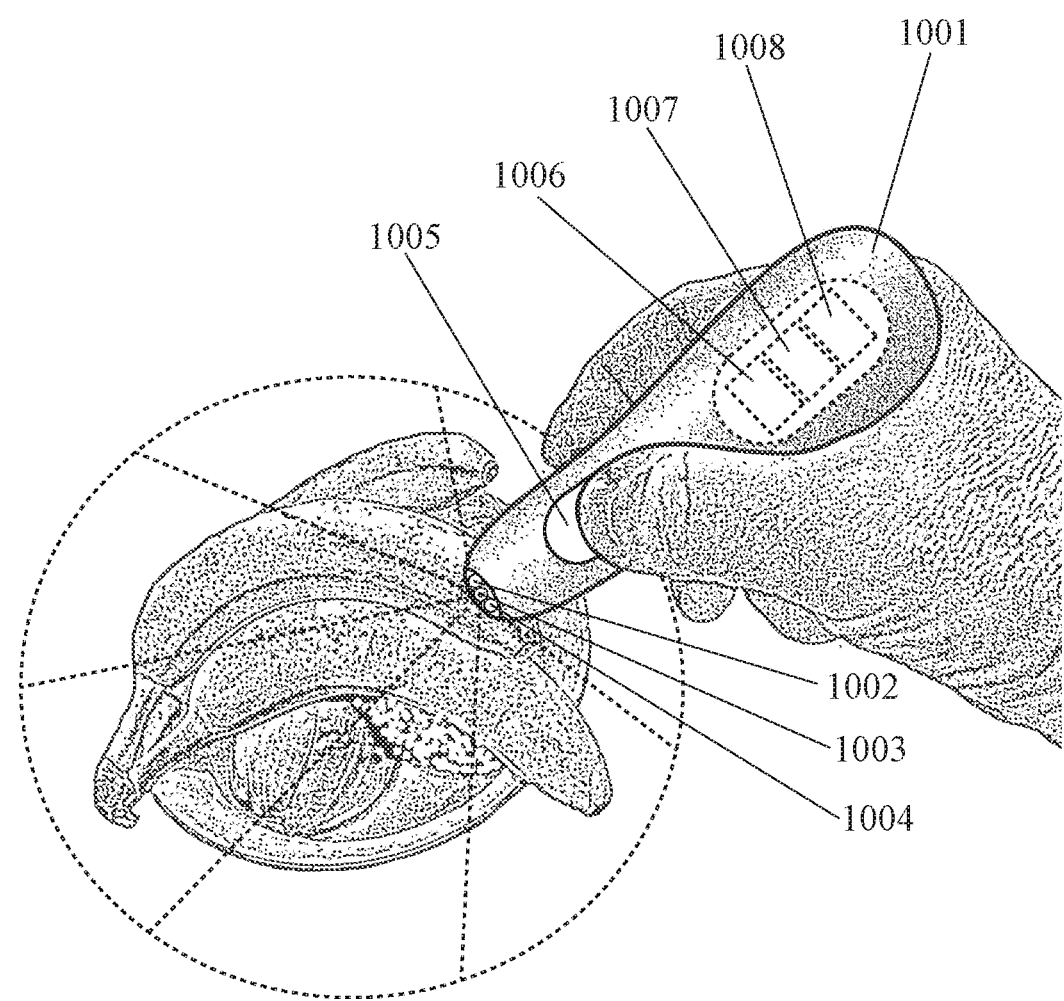

FIG. 1 shows a side/top-down view of the housing 1001 of this device being held by a person's hand over a bowl of fruit, wherein a beam of light from spectroscopic sensor 1002 (on the distal end of the device housing) is directed toward the fruit and reflected back from the fruit to the spectroscopic sensor. Changes in the spectrum of this beam of light are analyzed to determine the molecular composition of the fruit. FIG. 2 shows a side/top-down view of this same device, wherein a pattern of light 2001 is being projected onto the fruit from light pattern projector 1004. In an example, this projected light pattern can serve as a fiducial marker for estimating fruit size and quantity. FIG. 3 shows a side/top-down view of this same device, wherein camera 1003 is recording images (taking pictures) of the fruit. In an example, two or more of these component functions can occur simultaneously. Other components and design variations described in other portions of this disclosure and priority-linked disclosures can also be applied to these figures.

Figure 4:
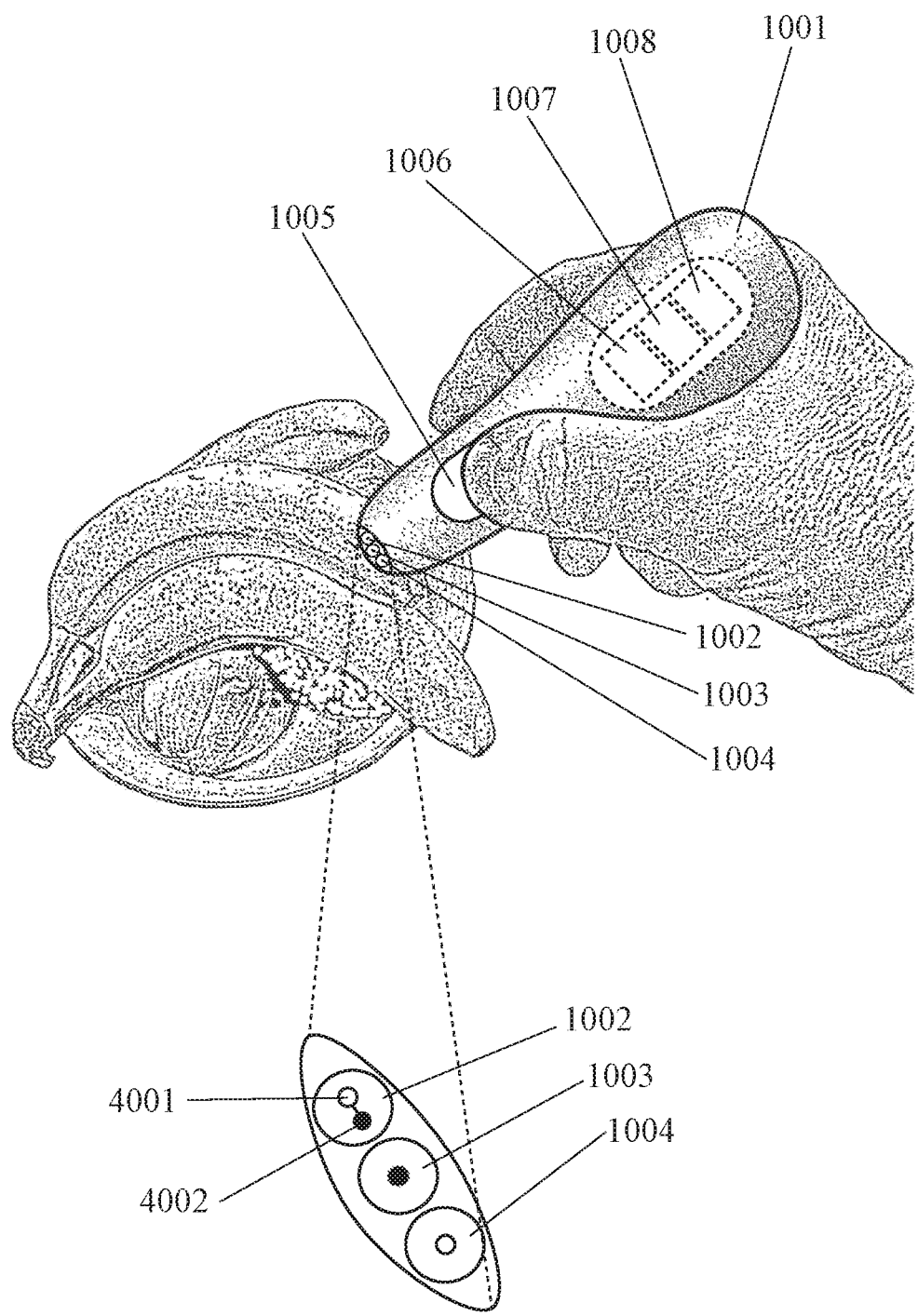

FIG. 4 shows a more detailed view of the device which was shown in FIGS. 1 through 3. The upper portion of FIG. 4 shows a side/top-down view of the housing 1001 of this device being held by a person's hand over a bowl of fruit. The lower portion of FIG. 4 shows an enlarged view of the distal end of this housing in order to show more details of the components located on the distal end. The upper portion of FIG. 4 shows device housing 1001, spectroscopic sensor 1002, camera 1003, light pattern projector 1004, button 1005, battery 1006, data processor 1007, and data transmitter/receiver 1008. The lower portion of FIG. 4 shows an enlarged view of the distal end of the device housing with spectroscopic sensor 1002 further comprising light energy emitter 4001 and light energy receiver 4002, camera 1003, and light pattern projector 1004. Other components and design variations described in other portions of this disclosure and priority-linked disclosures can also be applied to this figure.

Figure 5:
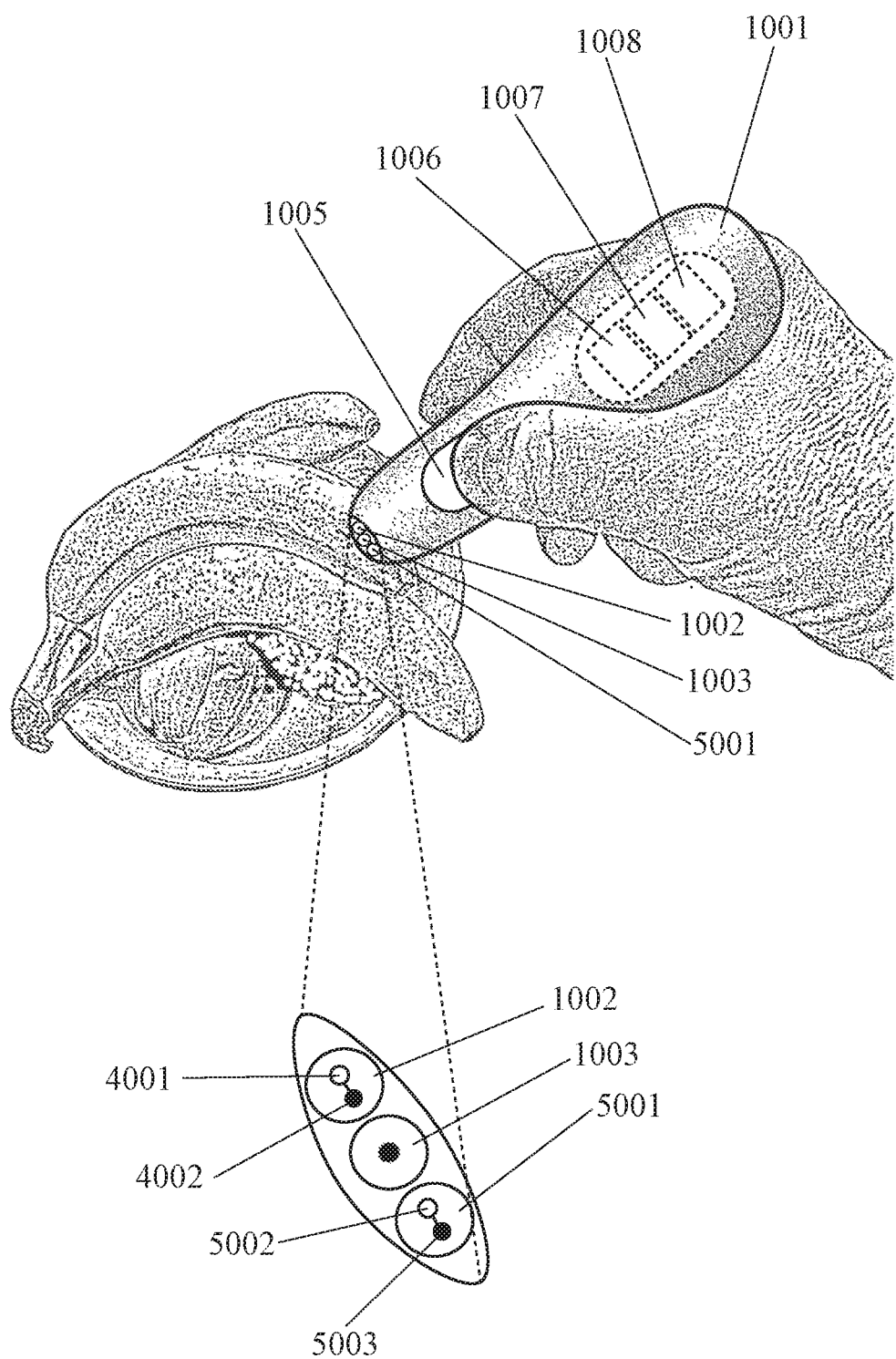
FIG. 5 shows a mobile device for food identification and quantification comprising a handheld arcuate housing with a spectroscopic sensor, a distance finder, and a camera on its distal end.

FIG. 5 shows another example of a mobile device for food identification and quantification. This example is like the one shown in FIG. 4 except that it has a distance finder instead of a light pattern projector. The upper portion of FIG. 5 shows a side/top-down view of the housing 1001 of this device being held by a person's hand over a bowl of fruit. The lower portion of FIG. 5 shows an enlarged view of the distal end of this housing in order to show more details of the components located on the distal end. The upper portion of FIG. 5 shows device housing 1001, spectroscopic sensor 1002, camera 1003, distance finder 5001, button 1005, battery 1006, data processor 1007, and data transmitter/receiver 1008. The lower portion of FIG. 5 shows an enlarged view of the distal end of the device housing with spectroscopic sensor 1002 further comprising first light energy emitter 4001 and first light energy receiver 4002, camera 1003, and distance finder 5001 further comprising second light energy emitter 5002 and second light energy receiver 5003. Other components and design variations described in other portions of this disclosure and priority-linked disclosures can also be applied to this figure.

FIG. 5 shows an example of a mobile device for food identification and quantification comprising: an arcuate housing 1001 which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; a spectroscopic sensor 1002, wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; a distance finder 5001, wherein the distance finder further comprises a second energy emitter and a second energy receiver, wherein the second energy emitter sends sound, light, or other electromagnetic energy from the distal half of the housing toward food, wherein the second energy receiver receives some of the energy sent by the second energy emitter after this energy has been reflected by the food, and wherein the angle, timing, or frequency of the reflected energy is used to measure the distance to the food; and a camera 1003 on the distal half of the housing, wherein the camera creates images of the food, and wherein the images of the food are analyzed in order to help identify the type of food and/or measure the quantity of food. The device in FIG. 5 further comprises a button 1005, battery 1006, data processor 1007, and data transmitter/receiver 1008. Other components and design variations described in other portions of this disclosure and priority-linked disclosures can also be applied to this figure.

Figure 6:
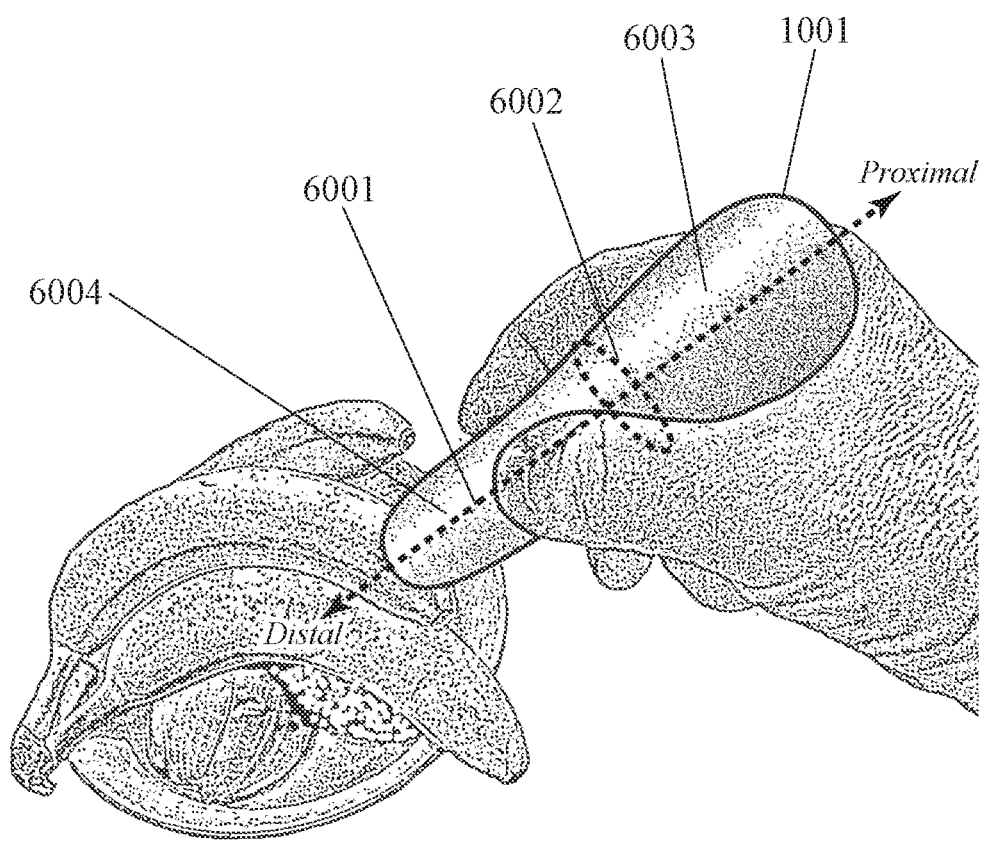
FIG. 6 illustrates the longitudinal axis, mid-point cross-section, distal half, and proximal half of the arcuate housing.

FIG. 6 shows an example of how the longitudinal axis, the mid-point cross-section, the distal half, and the proximal half of a device housing can be visualized. FIG. 6 shows a side/top-down view of the housing 1001 of this device being held by a person's hand over a bowl of fruit. The housing has a longitudinal axis 6001. There is a mid-point cross-section 6002 of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist. The proximal half 6003 of the housing is the portion of the housing which is proximal relative to the mid-point cross-section. The distal half 6004 of the housing is the portion of the housing which is distal relative to the mid-point cross-section.

Figure 7:
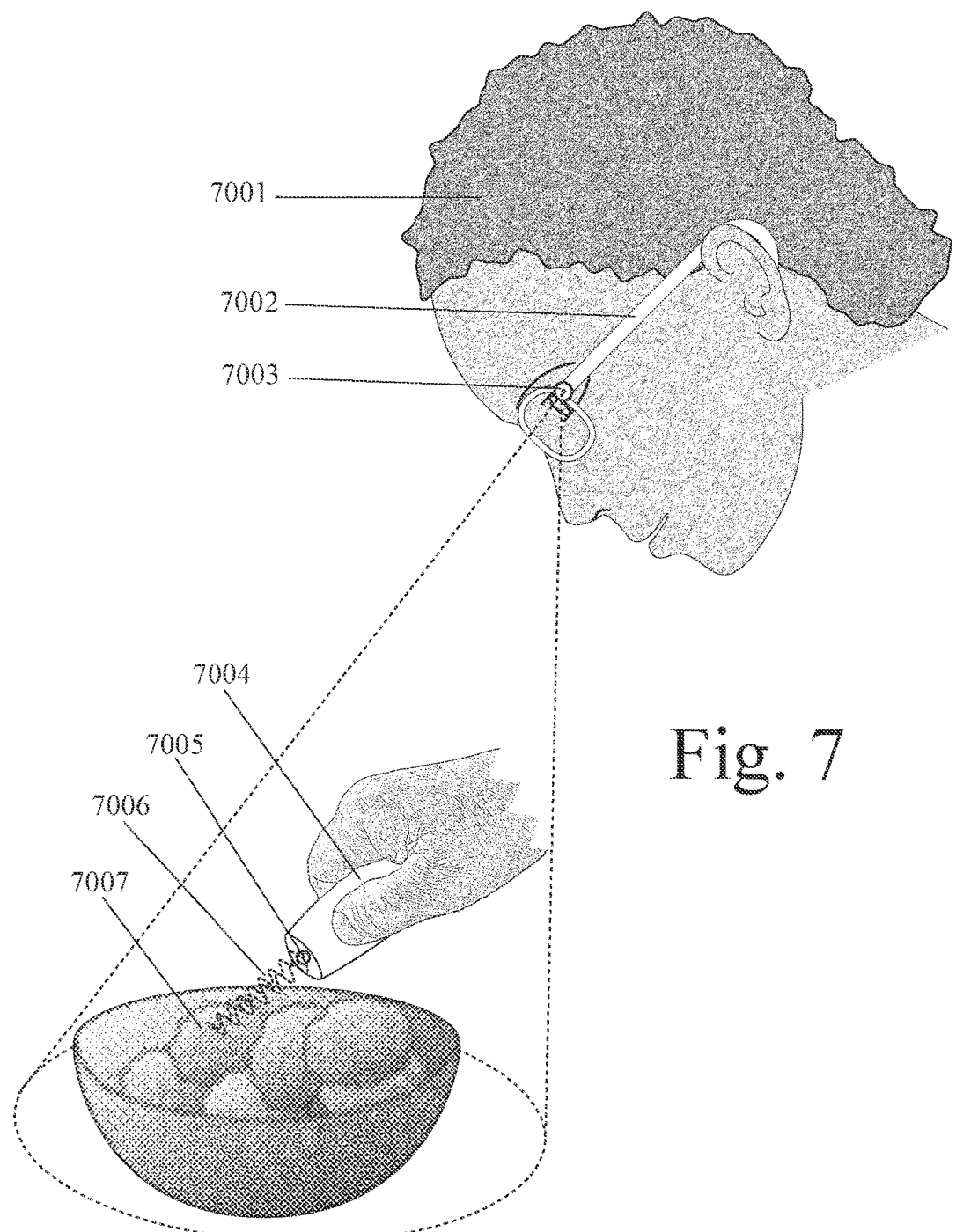
FIG. 7 shows a system for food identification and quantification comprising eyewear with a camera and a handheld arcuate housing with a spectroscopic sensor.

FIG. 7 shows an example of a system for food identification and quantification comprising: (A) eyewear 7002 which is configured to be worn by person 7001, wherein this eyewear further comprises a camera 7003, wherein the camera records images (takes pictures) of food 7007, and wherein the images of the food are analyzed in order to help identify the type of food and/or measure the quantity of food; and (B) a handheld arcuate housing 7004, which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate, wherein the housing further comprises a spectroscopic sensor 7005, wherein the spectroscopic sensor further comprises at least one first energy emitter and at least one first energy receiver, wherein a first energy emitter sends light beams 7006 from the distal half of the housing toward the food, wherein a first energy receiver receives some of the light beams after they have been reflected by the food, and wherein changes in the spectrum of the light beams caused by their reflection by the food are analyzed to help identify the type of food. Other components and design variations described in other portions of this disclosure and priority-linked disclosures can also be applied to this figure.

In an example, a mobile device for food identification and quantification can comprise: an arcuate housing which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; a spectroscopic sensor, wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; a light pattern projector, wherein the light pattern projector further comprises at least one second energy emitter, wherein the at least one second energy emitter projects a pattern of light from the distal half of the housing onto the food or within 12" of the food, and wherein the pattern of light is used to help measure the quantity of food and/or the distance to the food; and a camera on the distal half of the housing, wherein the camera creates images of the food including the projected pattern of light, and wherein the images of the food are analyzed in order to help identify the type of food and/or measure the quantity of food.

In an example, a mobile device for food identification and quantification can comprise: an arcuate housing which is configured to be held by a person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate; a spectroscopic sensor, wherein the spectroscopic sensor further comprises at least one first energy emitter and at least one first energy receiver, wherein a first energy emitter sends light beams from the distal half of the housing toward food, wherein a first energy receiver receives some of the light beams after they have been reflected by the food, and wherein changes in the spectrum of the light beams caused by their reflection by the food are analyzed to help identify the type of food; a distance finder, wherein the distance finder further comprises a second energy emitter and a second energy receiver, wherein the second energy emitter sends sound, light, or other electromagnetic energy from the distal half of the housing toward food, wherein the second energy receiver receives some of the energy sent by the second energy emitter after the energy has been reflected by the food, and wherein the angle, timing, or frequency of the reflected energy is used to measure the distance to the food; and a camera on the distal half of the housing, wherein the camera creates images of the food, and wherein the images of the food are analyzed in order to help identify the type of food and/or measure the quantity of food.

In an example, a system for food identification and quantification can comprise: eyewear which is configured to be worn by a person, wherein the eyewear further comprises a camera, wherein the camera records images of food, and wherein the images of the food are analyzed in order to help identify the type of food and/or measure the quantity of food; and a handheld arcuate housing, which is configured to be held by the person's thumb and index finger, wherein the housing has a longitudinal axis, wherein there is a mid-point cross-section of the housing which is a cross-sectional slice of the housing in a plane which is perpendicular to the longitudinal axis and which intersects the mid-point of the longitudinal axis, wherein proximal is defined as being closer to the person's wrist and distal is defined as being farther from the person's wrist, wherein a proximal half of the housing is the portion of the housing which is proximal relative to the mid-point cross-section, wherein a distal half of the housing is the portion of the housing which is distal relative to the mid-point cross-section, and wherein the perimeter of the mid-point cross-section is arcuate, wherein the housing further comprises a spectroscopic sensor, wherein the spectroscopic sensor further comprises at least one first energy emitter and at least one first energy receiver, wherein a first energy emitter sends light beams from the distal half of the housing toward the food, wherein a first energy receiver receives some of the light beams after they have been reflected by the food, and wherein changes in the spectrum of the light beams caused by their reflection by the food are analyzed to help identify the type of food.

I claim:

1. A mobile device for food identification and quantification comprising:
a housing which is configured to be held by a person's thumb and index finger;
wherein the housing further comprises a food probe which is inserted into food;
wherein the housing further comprises a spectroscopic sensor, wherein the spectroscopic sensor further comprises at least one first energy emitter and at least one first energy receiver, wherein a first energy emitter sends light beams toward the food, wherein a first energy receiver receives some of the light beams after they have been reflected by the food, and wherein changes in the spectrum of the light beams caused by their reflection by the food are analyzed to help identify the type of food;
and
wherein the housing further comprises a camera on the distal half of the housing, wherein the camera creates images of the food, and wherein the images of the food are analyzed in order to help identify the type of food and/or measure the quantity of food.

2. A system for food identification and quantification comprising:
augmented reality eyewear which is configured to be worn by a person, wherein the eyewear further comprises a camera, wherein the camera records images of food, and wherein the images of the food are analyzed in order to help identify the type of food and/or measure the quantity of food; and a handheld housing, which is configured to be held by the person's thumb and index finger, wherein the housing further comprises a spectroscopic sensor, wherein the spectroscopic sensor further comprises at least one first energy emitter and at least one first energy receiver, wherein a first energy emitter sends light beams toward the food, wherein a first energy receiver receives some of the light beams after they have been reflected by the food, and wherein changes in the spectrum of the light beams caused by their reflection by the food are analyzed to help identify the type of food; and a virtual pointer which the eyewear displays in the person's field of view at different locations on the food in order to direct where the person should place the spectroscopic sensor in order to take scans of the food.

3. A system for food identification and quantification comprising:

augmented reality eyewear which is configured to be worn by a person, wherein the eyewear further comprises a camera, wherein the camera records images of food, and wherein the images of the food are analyzed in order to help identify the type of food and/or measure the quantity of food; and a handheld housing, which is configured to be held by the person's thumb and index finger, wherein the housing further comprises a spectroscopic sensor, wherein the spectroscopic sensor further comprises at least one first energy emitter and at least one first energy receiver, wherein a first energy emitter sends light beams toward the food, wherein a first energy receiver receives some of the light beams after they have been reflected by the food, and wherein changes in the spectrum of the light beams caused by their reflection by the food are analyzed to help identify the type of food; and wherein the eyewear tracks where the person moves the spectroscopic sensor for food scans and links scan results from those locations with different portions or types of food identified by analysis of images of the food.

* * * * *